United States Patent [19]

Stevens et al.

[11] Patent Number: 5,753,682

[45] Date of Patent: May 19, 1998

[54] IMIDAZOLE LIPOXYGENASE INHIBITORS

[75] Inventors: Rodney W. Stevens; Takashi Mano; Kazuo Ando, all of Aichi, Japan

[73] Assignee: Pfizer Inc., New York, N.Y.

[21] Appl. No.: 553,546

[22] PCT Filed: May 25, 1994

[86] PCT No.: PCT/JP94/00836

§ 371 Date: May 6, 1996

§ 102(e) Date: May 6, 1996

[87] PCT Pub. No.: WO94/29299

PCT Pub. Date: Dec. 22, 1994

[30] Foreign Application Priority Data

Jun. 14, 1993 [JP] Japan .................. 5-142206

[51] Int. Cl.$^6$ .............. C07D 233/60; C07D 405/12; C07D 405/14; A61K 31/415

[52] U.S. Cl. .............. 514/341; 514/399; 546/274.1; 548/311.1; 548/315.4

[58] Field of Search .............. 548/311.1, 315.4, 548/342.5, 343.1, 343.5; 546/274.1; 514/341, 399

[56] References Cited

U.S. PATENT DOCUMENTS

| | | | |
|---|---|---|---|
| 5,223,525 | 6/1993 | Wu et al. | 514/398 |
| 5,246,957 | 9/1993 | Cozzi et al. | 514/397 |
| 5,276,037 | 1/1994 | Dowell et al. | 514/253 |
| 5,403,859 | 4/1995 | Edwards et al. | 514/450 |

*Primary Examiner*—Mukund J. Shah
*Assistant Examiner*—Deepak R. Rao
*Attorney, Agent, or Firm*—Peter C. Richardson; Paul H. Ginsburg; Garth Butterfield

[57] ABSTRACT

Certain novel imidazole derivatives having the ability to inhibit the lipoxygenase enzyme and having formula (I), wherein Y is hydrogen, $C_1$–$C_8$ alkyl, halosubstituted $C_1$–$C_4$ alkyl, phenyl, substituted phenyl, $C_7$–$C_{14}$ phenylalkyl, $C_7$–$C_{14}$ (substituted phenyl)alkyl, pyridyl, substituted pyridyl, $C_6$–$C_{13}$ pyridylalkyl or $C_6$–$C_{13}$ (substituted pyridyl)alkyl, wherein each substituent is independently halo, nitro, cyano, $C_1$–$C_4$ alkyl, $C_1$–$C_4$ alkoxy, halosubstituted $C_1$–$C_4$ alkyl, halosubstituted $C_1$–$C_4$ alkoxy, $NR^4R^5$, $CO_2R^4$ or $CONR^4R^5$, wherein $R^4$ and $R^5$ are each, independently, hydrogen or $C_1$–$C_6$ alkyl; $Ar^1$ and $Ar^2$ are each, independently, phenylene, mono-substituted phenylene or di-substituted phenylene, wherein the substituents are, independently, halo, $C_1$–$C_4$ alkyl, $C_1$–$C_4$ alkoxy, halosubstituted $C_1$–$C_4$ alkyl or halo-substituted $C_1$–$C_4$ alkoxy; X and $X^1$ are each, independently, O, S, SO or $SO_2$; R' is hydrogen or $C_1$–$C_4$ alkyl; and $R^2$ and $R^3$ are each, independently, methylene, ethylene or propylene. These compounds are useful for the treatment of disease states such as bronchial asthma, skin disorders and arthritis in mammals, and as the active ingredient in pharmaceutical compositions for treating such conditions.

15 Claims, No Drawings

IMIDAZOLE LIPOXYGENASE INHIBITORS

TECHNICAL FIELD

This application is a 371 of PCT/JP94/00836 filed on May 25, 1994.

This invention relates to novel imidazole compounds. The compounds of the present invention inhibit the action of the lipoxygenase enzyme and are useful in the treatment or alleviation of inflammatory diseases, allergy and cardiovascular diseases in mammals, especially human subjects. This invention also relates to pharmaceutical compositions comprising such compounds.

BACKGROUND ART

Arachidonic acid is known to be the biological precursor of several groups of biologically active endogenous metabolites. The first step in the metabolism of arachidonic acid is its release from membrane phospholipids, via the action of phospholipase A2. Arachidonic acid is then metabolized either by cyclooxygenase to produce prostaglandins including prostacyclin, and thromboxanes or by lipoxygenase to generate hydroperoxy fatty acids which may be further converted to the leukotrienes.

The leukotrienes are extremely potent substances which elicit a wide variety of biological effects, often in the nanomolar to picomolar concentration range. The peptide leukotrienes ($LTC_4$, $LTD_4$, $LTE_4$) are important bronchoconstrictors and vasoconstrictors, and also cause plasma extravasation by increasing capillary permeability. $LTB_4$ is a potent chemotactic agent, enhancing the influx of leukocytes and inducing their subsequent degranulation at the site of inflammation. A pathophysiological role for leukotrienes has been implicated in a number of human disease states including asthma, rheumatoid arthritis and gout, psoriasis, adult respiratory distress syndrome (ARDS), inflammatory bowel diseases (e.g. Crohn's disease), endotoxin shock, and ischemia-induced myocardial injury. Any agent that inhibits the action of lipoxygenases is expected to be of considerable therapeutic value for the treatment of acute and chronic inflammatory conditions.

Several review articles on lipoxygenase inhibitors have been published. See J. A. Salmon and L. G. Garland: *Progress in Drug Research*, 1991, 37, pp9–90 (Birkhauser Verlag), H. Masamune and L. S. Melvin, Sr.: *Annual Reports in Medicinal Chemistry*, 1989, 24, pp71–80 (Academic Press), and B. J. Fitzsimmons and J. Rokach: *Leukotrienes and Lipoxygenases*, 1989, pp 427–502 (Elsevier).

Compounds of similar structure to the compounds of the present invention are disclosed in EP 0 488 602 A1, EP 0 409 413 A2 and EP 0 375 404 A2.

The present inventors have worked to prepare compounds capable of inhibiting the action of lipoxygenase and after extensive research they have succeeded in synthesizing a series of compounds as disclosed in detail herein.

BRIEF DISCLOSURE OF THE INVENTION

The present invention provides novel imidazole compounds of the following chemical formula I

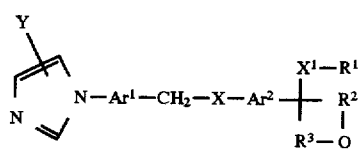

and the pharmaceutically-acceptable salts thereof, wherein

Y is hydrogen, $C_1$–$C_8$ alkyl, halosubstituted $C_1$–$C_4$ alkyl, phenyl, substituted phenyl, $C_7$–$C_4$ phenylalkyl, $C_7$–$C_4$ (substituted phenyl)alkyl, pyridyl, substituted pyridyl, $C_6$–$C_{13}$ pyridylalkyl or $C_6$–$C_{13}$ (substituted pyridyl)alkyl, wherein each substituent is independently halo, nitro, cyano, $C_1$–$C_4$ alkyl, $C_1$–$C_4$ alkoxy, halosubstituted $C_1$–$C_4$ alkyl, halosubstituted $C_1$–$C_4$ alkoxy, $NR^4R^5$, $CO_2R^4$ or $CONR^4R^5$, wherein $R^4$ and $R^5$ are each, independently, hydrogen or $C_1$–$C_6$ alkyl;

$Ar^1$ and $Ar^2$ are each, independently, phenylene, monosubstituted phenylene or di-substituted phenylene, wherein the substituents are, independently, halo, $C_1$–$C_4$ alkyl, $C_1$–$C_4$ alkoxy, halo-substituted $C_1$–$C_4$ alkyl or halosubstituted $C_1$–$C_4$ alkoxy;

X and $X^1$ are each, independently, O, S, SO or $SO_2$;

$R^1$ is hydrogen or $C_1$–$C_4$ alkyl; and $R^2$ and $R^3$ are each, independently, methylene, ethylene or propylene.

A preferred group of compounds of this invention consists of compounds of the formula I, wherein Y is at the 2-position of the imidazole ring; $Ar^1$ is 1,4-phenylene or monosubstituted 1,4-phenylene; $Ar^2$ is 1,3-phenylene or monosubstituted 1,3-phenylene; X is O or S; $X^1$ is O; and $R^2$ and $R^3$ are each ethylene. Within this preferred group, particularly preferred compounds are those in which Y is 2-alkyl; $Ar^1$ is 1,4-phenylene or 2-fluoro-1,4-phenylene; $Ar^2$ is 1,3-phenylene, 2-fluoro-1,3-phenylene or 5-fluoro-1,3-phenylene; X is O; and $R^1$ is methyl. Most particularly, Y is 2-methyl.

A second preferred group of compounds of this invention consists of the compounds of formula I, wherein Y is 2-alkyl; $Ar^1$ is 1,4-phenylene or 2-fluoro-1,4-phenylene; $Ar^2$ is 1,3-phenylene, 2-fluoro-1,3-phenylene or 5-fluoro-1,3-phenylene; X is O; $X^1$ is S; $R^1$ is methyl; and $R^2$ and $R^3$ are each ethylene. Within this second preferred group, especially preferred are compounds in which Y is 2-methyl.

A third preferred group of compounds of this invention consists of the compounds of formula I, wherein Y is 2-alkyl; $Ar^1$ is 1,4-phenylene or mono-substituted 1,4-phenylene; $Ar^2$ is 2,5-difluoro-1,3-phenylene; X and $X^1$ are each O; $R^1$ is methyl; and $R^2$ and $R^3$ are each ethylene. Within this third preferred group, especially preferred are compounds in which Y is 2-methyl.

DETAILED DESCRIPTION OF THE INVENTION

In this application, the following terms are used.

The term "halo" is used to mean fluoro, chloro, bromo or iodo.

The term "alkyl" is used to mean straight or branched hydrocarbon chain radicals including, but not limited to, methyl, ethyl, n-propyl, isopropyl, n-butyl, and the like.

The term "alkoxy" is used herein to mean —$OR^5$ ($R^5$ is alkyl) including, but not limited to, methoxy, ethoxy, n-propoxy, isopropoxy, n-butoxy and the like.

The term "halo-substituted alkyl" refers to an alkyl radical as described above substituted with one or more halogens including, but not limited to, chloromethyl, bromoethyl, trifluoromethyl and the like. The preferred halo-substituted alkyl group is trifluoromethyl.

The term "halo-substituted alkoxy" is used to mean an alkoxy radical as described above substituted with one or more halogens including, but not limited to, chloromethoxy, bromoethoxy, difluoromethoxy, trifluoromethoxy and the like. The preferred halo-substituted alkoxy group is trifluoromethoxy.

The terms "substituted phenyl" and "substituted pyridyl" are used herein to mean phenyl groups and pyridyl groups having up to three substituents, and these substituents can either be the same or different. However, monosubstituted phenyl and monosubstituted pyridyl are preferred.

In the term "$C_7$–$C_{14}$ (substituted phenyl)alkyl," the range $C_7$–$C_{14}$ refers to the number of carbons in the phenyl and alkyl groups, and does not include any carbons in the substituents. Similarly in "$C_6$–$C_{13}$ (substituted pyridyl)alkyl," the range $C_6$–$C_{13}$ refers only to the pyridyl and alkyl groups.

General Synthesis

A compound of formula I, or a pharmaceutically acceptable salt thereof, may be prepared by any synthetic procedure applicable to structurally-related compounds known to those skilled in the art. For example, the compound of the formula I is prepared according to the reaction outlined in Scheme 1.

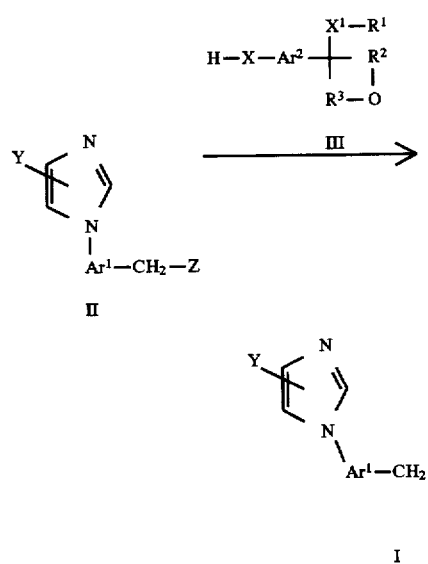

wherein Z is OH or a displaceable group, and Y, $Ar^1$, $Ar^2$, X, $X^1$, $R^1$, $R^2$, and $R^3$ have the same meanings as defined above.

Method A

In one embodiment, a compound of formula II wherein Z is a hydroxyl group is coupled with a compound of formula III wherein X is O by dehydration. A variety of dehydrating agents can be used, but a convenient way of carrying out this transformation is to use diethyl azodicarboxylate and triphenylphosphine in a reaction-inert solvent. Suitable solvents are dichloromethane, tetrahydrofuran and toluene. Reaction temperatures are preferably in the range of 0° C. through to room temperature, but if necessary, lower or higher temperature can be employed. Reaction time is in general from several minutes to several hours.

Method B

Alternatively, a compound of formula II wherein Z is a displaceable group (a leaving group) is coupled with a compound of formula III, preferably in the presence of a suitable base. A suitable displaceable group Z is a halo or sulfonyloxy group; for example, chloro, bromo, iodo, trifluoromethanesulfonyloxy, methanesulfonyloxy or p-toluenesulfonyloxy group, all readily accessible from the corresponding alcohol by conventional methods. Preferred base for the coupling reaction is, for example, an alkaline metal or alkaline earth metal hydroxide, alkoxide, carbonate or hydride such as sodium hydroxide, potassium hydroxide, sodium methoxide, sodium ethoxide, potassium tert-butoxide, sodium carbonate, potassium carbonate, sodium hydride or potassium hydride, or an amine such as triethylamine, diisopropylethylamine or dimethylaminopyridine. Preferred reaction-inert solvents include, for example, acetone, acetonitrile, dichloromethane, N,N-dimethylacetamide, N,N-dimethylformamide, dimethyl sulfoxide or tetrahydrofuran. Reaction temperatures are preferably in the range of room temperature to reflux temperature of solvent, but if necessary, lower or higher temperature can be employed. Reaction time is in general from a few hours to several days.

For the preparation of those compounds in formula I wherein X is a sulfinyl or sulfonyl group, a compound of formula I wherein X is S may be oxidized by conventional methods. A suitable oxidizing agent is, for example, hydrogen peroxide, a peracid such as m-chloroperoxybenzoic or peroxyacetic acid, an alkaline metal peroxysulfate such as potassium peroxymonosulfate or the like. Preferred reaction-inert solvents include, for example, acetone, dichloromethane, chloroform, tetrahydrofuran or water. Reaction temperatures are preferably in the range 0° C. to room temperature, but if necessary, lower or higher temperature can be employed. Reaction time is in general from a few minutes to several hours.

The starting material of formula III may be obtained by conventional procedures known to those skilled in the art. For example, as described in J. Med. Chem., 1992, 35, 2600–2609 and EP 0 375 404 A2.

The starting material of formula II may be obtained by conventional procedures known to those skilled in the art. For example, the compound of the formula II is prepared according to the reaction outlined in Scheme 2.

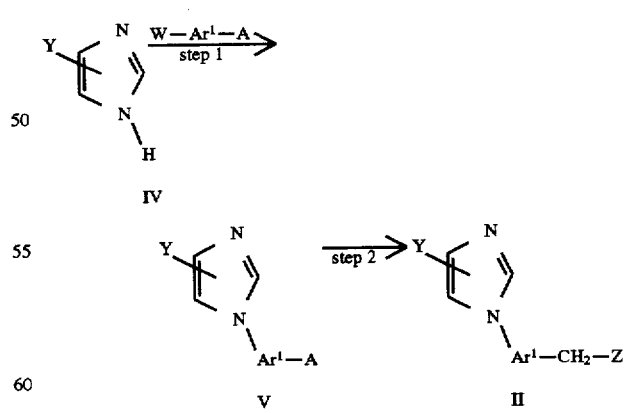

wherein W is a displaceable group, A is a suitable electron withdrawing group, and Y, $Ar^1$, and Z have the same meanings as defined above.

In the first step, a compound of formula IV is coupled, preferably in the presence of a suitable base, with a compound of formula W-Ar¹-A to afford a compound of formula V. A suitable displaceable group W is a halo or sulfonyloxy group, for example, fluoro, chloro, bromo, iodo or trifluoromethanesulfonyloxy group. A suitable electron withdrawing group A is, for example, cyano, carboxaldehyde, carboxylic acid or carboxylic ester. Preferred base for the coupling reaction is, for example, an alkaline metal or alkaline earth metal hydroxide, alkoxide, carbonate or hydride such as sodium hydroxide, potassium hydroxide, sodium methoxide, sodium ethoxide, potassium tert-butoxide, sodium carbonate, potassium carbonate, sodium hydride or potassium hydride, or alkyl metal such as n-butyllithium, ethylmagnesium bromide or the like. Preferred reaction-inert solvents include, for example, methanol, ethanol, pyridine, N,N-dimethylformamide, dimethyl sulfoxide, N-methylpyrrolidin-2-one, N,N-dimethylacetamide, or tetrahydrofluran. Reaction temperatures are preferably in the range of 50° C. through to 150° C., but if necessary, lower or higher temperature can be employed. Reaction time is in general from a few hours to several days. Conveniently the reaction may be conducted in the presence of a suitable catalyst, for example, tetrakis (triphenylphosphine)-palladium, bis(triphenylphosphine)-palladium(II) chloride, cuprous oxide, cuprous iodide, cuprous chloride or cuprous bromide.

A compound of formula V is transformed to a compound of formula II wherein Z is hydroxyl group by standard procedure well known to those skilled in the art. Thus, in step 2, a compound of formula II is readily prepared by reduction with conventional reducing agents such as sodium borohydride, lithium aluminum hydride, diisobutylaluminum hydride, borane-tetrahydrofuran complex, borane-methyl sulfide complex or the like.

The products which are addressed in the aforementioned general syntheses and illustrated in the experimental examples herein may be isolated by standard methods and purification can be achieved by conventional means known to those skilled in the art, such as distillation, recrystallization and chromatography techniques.

The compounds of the present invention which contain one or more asymmetric centers are capable of existing in various stereoisomeric forms. All such individual forms, and mixtures thereof, are included within the scope of this invention. The various isomers can be obtained by standard methods. For example, racemic mixtures can be separated into the individual enantiomers by standard resolution techniques. Individual diastereomers can be obtained by stereoselective synthesis, or by separation of mixtures by fractional crystallization or chromatography techniques.

Insofar as the compounds of the present invention are basic compounds, they are all capable of forming a wide variety of acid addition salts with various inorganic and organic acids. The acid addition salt of the novel compounds of the invention are readily prepared by contacting said compound with a chosen mineral or organic acid in an aqueous solvent medium or in a suitable organic solvent, such as methanol or ethanol. The desired solid salt may then be obtained by precipitation or by careful evaporation of the solvent.

The acids which are used to prepare the pharmaceutically acceptable acid addition salts of the aforementioned compounds of this invention are those which form non-toxic acid addition salts, such as the hydrochloride, hydrobromide, hydroiodide, nitrate, sulfate, acetate, fumarate, tartrate, succinate, maleate, gluconate, saccharate, benzoate, methanesulfonate, benzenesulfonate, p-toluenesulfonate and pamoate (i.e., 1,1'-methylene-bis-(2-hydroxy-3-naphthoate)) salts.

The compounds of the invention which have also acidic groups are capable of forming base salts with various pharmaceutically acceptable cations. Examples of such salts include the alkali metal or alkaline earth metal salts and particularly, the sodium and potassium salts. These salts are all prepared by conventional techniques. The chemical bases which are used as reagents to prepare the pharmaceutically acceptable base salts of this invention are those which form non-toxic base salts. These particular non-toxic base salts include those derived from such pharmaceutically acceptable cations as sodium, potassium, calcium and magnesium, etc. These salts can easily be prepared by treating the aforementioned compounds with an aqueous solution containing the desired pharmaceutically acceptable cation, and then evaporating the resulting solution to dryness, preferably under reduced pressure. Alternatively, they may also be prepared by mixing lower alkanoic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum production of yields of the desired final product.

The compounds of the present invention inhibit the activity of the 5-lipoxygenase enzyme. This inhibition can be demonstrated in vitro in assays using rat peritoneal cavity (RPC) resident cells (*Japanese Journal of Inflammation:* 1987, 7, 145–150) and heparinised human whole blood (HWB) (*Br. J. of Pharmacol.:* 1990, 99, 113–118) both of which determine the effect of said compounds on the metabolism of arachidonic acid. All of the following examples tested in the aforementioned assays were shown to possess the efficacy of inhibiting lipoxygenase activity. Some preferred compounds indicated low $IC_{50}$ values, in the range of 0.001 to 1 µM, with respect to lipoxygenase activity.

The ability of the compounds of the present invention to inhibit lipoxygenase enzyme makes them useful for controlling the symptoms induced by the endogenous metabolites arising from arachidonic acid in a mammalian subject, especially a human subject. The compounds are therefore valuable in the prevention and treatment of such disease states in which the accumulation of arachidonic acid metabolites are the causative factor; e.g. allergic bronchial asthma, skin disorders, rheumatoid arthritis and osteoarthritis.

In particular, the compounds of the present invention and their pharmaceutically acceptable salts are of use in the treatment or alleviation of inflammatory diseases in a human subject.

For treatment of the various conditions described above, the compounds and their pharmaceutically acceptable salts can be administered to a human subject either alone, or preferably in combination with pharmaceutically acceptable carriers or diluents in a pharmaceutical composition according to standard pharmaceutical practice. The compounds can be administered orally or parenterally in conventional fashion.

When the compounds are administered to a human subject for the prevention or treatment of an inflammatory disease, the oral dose range will be from about 0.1 to 10 mg/kg per body weight of the subject to be treated per day, preferably from about 0.1 to 4 mg/kg per day in single or divided doses. If parenteral administration is desired, then an effective dose will be from about 0.05 to 5 mg/kg per body weight of the subject to be treated per day. In some instances it may be necessary to use dosages outside these limits, since the dosages will necessarily vary according to the age, weight and response of the individual patient as well as the severity of the patient's symptoms and the potency of the particular compound being administered.

For oral administration, the compounds of the invention and their pharmaceutically acceptable salts can be administered, for example, in the form of tablets, powders, lozenges, syrups or capsules or as an aqueous solution or suspension. In the case of tablets for oral use, carriers which are commonly used include lactose and corn starch. Further lubricating agents such as magnesium stearate are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added. For intramuscular, intraperitoneal, subcutaneous and intravenous use, sterile solutions of the active ingredient are usually prepared and the pH of the solutions should be suitably adjusted and buffered. For intravenous use, the total concentration of solute should be controlled to make the preparation isotonic.

In addition, particularly for the treatment of asthma, the compounds of formula I of this invention can be administered to a human subject by inhalation. For this purpose they are administered as a spray or mist, according to standard practice.

The present invention is illustrated by the following examples. However, it should be understood that the invention is not limited to the specific details of these examples. Proton nuclear magnetic resonance spectra (NMR) were measured at 270 MHz unless otherwise indicated and peak positions are expressed in parts per million (ppm) downfield from tetramethylsilane. The peak shapes are denoted as follows: s—singlet, d—doublet, t—triplet, q—quartet, quint—quintet, m—multiplet, br—broad.

EXAMPLE 1

4-[3-[4-(1-Imidazolyl)benzyloxy]phenyl]-4-methoxy-3,4,5,6-tetrahydro-2H-pyran

To a stirred solution of 4-(1-imidazolyl)benzyl alcohol (Eur. J. Med. Chem., 1992, 27, 219) (0.87 g, 5.0 mmol), 4-(3-hydroxyphenyl)-4-methoxy-3,4,5,6-tetrahydro-2H-pyran (J. Med. Chem., 1992, 35, 2600) (1.03 g, 4.9 mmol) and triphenylphosphine (1.55 g, 5.9 mmol) in THF (30 ml) cooled to 0° C. was added dropwise a solution of diethyl azodicarboxylate (DEAD) (1.03 g, 12.0 mmol) in THF (10 ml) over 20 min under a nitrogen atmosphere. After completion of addition, the mixture was stirred at 0° C. for 30 min and allowed to warm to room temperature, and then volatiles were removed under reduced pressure. Chromatographic purification of the residue (SiO$_2$, 230 g; gradient elution, 15% to 30% acetone in dichloromethane) provided 0.27 g of the title compound as a gum, which solidified on standing at room temperature. Fractions contaminated with triphenylphosphine oxide were combined, concentrated to dryness, solidified by triturating with diisopropyl ether and recrystallized from diisopropyl ether / ethyl acetate to provide 0.16 g of the title compound. Combined solids were further purified by recrystallization from diisopropyl ether / ethyl acetate afforded the title compound as tiny colorless needles (0.30 g, 17%).

m.p.: 129°–130.5° C.

IR (KBr) cm$^{-1}$: 2960, 2875, 1607, 1579, 1524, 1480, 1306, 1281, 1251, 1073, 1061, 1026.

$^1$H NMR (CDCl$_3$) δ: 7.78 (t, 1H, J=1 Hz), 7.56 (d, 2H, J=8 Hz), 7.43 (d, 2H, J=8 Hz), 7.32 (t, 1H, J=8 Hz), 7.28 (dd, 1H, J=1, 8 Hz), 7.22 (t, 1H, J=1 Hz), 7.08–6.98 (m, 2H), 6.94–6.88 (in, 1H), 5.12 (s, 2H), 3.92–3.81 (m, 4H), 2.98 (s, 3H), 2.10–1.92 (m, 4H).

Analysis Calculated for C$_{22}$H$_{24}$N$_2$O$_3$: C, 72.51; H, 6.64; N, 7.69.

Found: C, 72.37; H, 6.74; N, 7.66.

EXAMPLE 2

4-Methoxy-4-[3-[4-(2-methylimnidazol-1-yl)benzyloxy]phenyl]3,4,5,6-tetrahydro-2H-pyran a. 4(2-Methylimidazol-1-yl)benzyl alcohol To a suspension of NaH (0.612 g, 15.3 mmol : 60% suspension of mineral oil) of in dry DMF (10 ml) cooled to 10° C. was added a DMF (8 ml) solution of 2-methylimidazole (1.23 g, 15 mmol) under a nitrogen atmosphere, and the mixture was stirred for 30 min at room temperature. 4-Fluorobenzaldehyde (1.90 g, 15.3 mmol) was added to the reaction mixture, and the resulting solution was stirred for 14 h. The reaction mixture was poured into an ice-cold saturated aqueous NH$_4$Cl solution (100 ml) and extracted with ethyl acetate (100 ml×2). The organic layer was washed with water (100 ml) and brine (80 ml), dried over MgSO$_4$ and the solvent removed under reduced pressure. The resultant residue was purified by column chromatography (SiO$_2$; hexane:ethyl acetate=1:1 then ethyl acetate) to give crude 4-(2-methylimidazol-1-yl)-benzaldehyde (1.0 g), which was used without further purification.

To a stirred solution of the crude 4-(2-methylimidazol-1-yl)benzaldehyde (1.0 g) in methanol(15 ml) cooled to 0° C. was added NaBH$_4$ (0.2 g, 5.2 mmol) in portions over 15 min and the whole stirred for 1 h. A saturated aqueous NH$_4$Cl solution (50 ml) was added to the reaction mixture and the whole extracted with ethyl acetate (100 ml×2). The organic layer was washed with water (100 ml), brine (50 ml), dried over MgSO$_4$, and solvent removed under reduced pressure. The crude product was washed with an Et$_2$O/ethyl acetate mixture (3:1, 15 ml) to give the title compound (0.51 g, 50 %) as a white powder. $^1$H NMR (CDCl$_3$) δ: 7.5 (d, 2H, J=8 Hz), 7.28 (d, 2H, J=8 Hz), 7.01 (d, 1H, J=1 Hz), 6.99 (d, 1H, J=1 Hz), 4.78 (s, 2H), 2.35 (s, 3H).

b. 4-Methoxy-4-[3-[4-(2-methylimidazol-1-yl)benzyloxy]phenyl]-3,4,5,6 -tetrahydro-2H-pyran The title compound was prepared from 4-(2-methylimidazol-1-yl)benzyl alcohol and 4-(3-hydroxyphenyl)-4-methoxy-3,4,5,6-tetrahydro-2H-pyran according to the procedure described for 4-[3-[4-(1-imidazolyl)benzyloxy]phenyl]-4-methoxy-3,4,5,6-tetrahydro-2H-pyran. (Example 1)

m.p.: 135.5°–137 ° C.

IR (KBr) cm$^{-1}$: 1520, 1416, 1248, 1073.

$^1$H NMR (CDCl$_3$) δ: 7.57 (d, 2H, J=8 Hz), 7.30–7.36 (m, 3H), 7.00–7.07 (m, 4H), 6.93 (ddd, 1H, J=8, 3, 1 Hz), 5.14 (s, 2H), 3.82–3.91 (m, 4H), 2.98 (s, 3H), 2.38 (s, 3H), 1.92–2.09 (m, 4H).

EXAMPLE 3

4-Methoxy-4-[3-[4-(4-methylimidazol-1-yl)benzyloxy]phenyl]-3,4,5,6-tetrahydro-2H-pyran The title compound was prepared using 4-methylimidazole and 4-fluorobenzaldehyde according to the procedure as described for 4-methoxy-4-[3-[4-(2-methylimidazol- 1-yl)benzyloxy]phenyl]-3,4,5,6-tetrahydro-2H-pyran (Example 2).

m.p.: 120°–121° C.

IR (KBr) cm$^{-1}$: 1525, 1251, 1076.

$^1$H NMR (CDCl$_3$)δ: 7.76 (d, 1H, J=1 Hz), 7.55 (d, 2H, J=9 Hz), 7.39 (d, J=9 Hz), 7.32 (t, 1H, J=8 Hz), 7.00–7.26 (m,

3H), 6.91 (dd, 1H, J=8, 2 Hz), 5.11 (s, 2H), 3.82–3.87 (m, 4H), 2.98 (s, 3H), 2.31 (s, 3H), 1.92–2.04 (m, 4H).

EXAMPLE 4

4-Methoxy-4-[3-[4-(2-phenylimidazol-1-yl)benzyloxy]phenyl]-3,4,5,6-tetrahydro-2H-pyran a. 4-(2-Phenylimidazol-1-yl)benzonitrile A mixture of 4-fluorobenzonitrile (3.63 g, 30 mmol), 2-phenylimidazole (3.72 g, 30 mmol) and anhydrous $K_2CO_3$ (4.15 g, 30 mmol) in dry DMSO (30 ml) was heated at 100° C. for 20 hours under a nitrogen atmosphere. After cooling to room temperature, the reaction mixture was poured into an ice-cold saturated aqueous $NH_4Cl$ (100 ml) solution and the whole extracted with $Et_2O$ (150 ml×2). The combined extracts was washed with water (100 ml), brine (80 ml), dried over $MgSO_4$ and solvent removed under reduced pressure. The resultant residue was purified by column chromatography ($SiO_2$; dichloromethane:ethyl acetate:ethanol=20:1:1) to afford title compound (3.61 g, 49%).

IR (KBr) $cm^{-1}$: 2220.

$^1H$ NMR ($CDCl_3$) δ: 7.74 (d, 2H, J=8 Hz), 7.27–7.38 (m, 8H), 7.20 (s, 1H).

b. 4-(2-Phenylimidazol-1-yl)benzyl alcohol

To a solution of 4-(2-phenylimidazol-1-yl)benzonitrile (3.2 g, 13 mmol) in dichloromethane (30 ml) and toluene (20 ml) cooled to −78° C. was added dropwise diisobutylaluminum hydride (13 ml, 13 mmol: 1.02M solution in toluene) under a nitrogen atmosphere and the whole stirred at this temperature for 1.5 h. Saturated aqueous $NH_4Cl$ solution (20 ml) was then added carefully to the reaction mixture, and the whole allowed to warm to room temperature. The resulting gelatinous mixture was filtered through a pad of celite, washing with ethyl acetate (200 ml). The filtrate was washed with 0.3N HCl solution (100 ml), water (200 ml) and brine (100 ml), and the organic layer dried over $MgSO_4$. Removal of solvent under reduced pressure provided crude product (2.5 g) which was dissolved in methanol (30 ml) and cooled to 0° C. $NaBH_4$ (0.3 g, 8 mmol) was added in portions and the reaction mixture stirred for 30 min. Saturated aqueous $NH_4Cl$ solution (30 ml) was added to the reaction mixture and the whole extracted with ethyl acetate (20 ml×3). The organic layer was washed with water (10 ml), brine (10 ml), dried over $MgSO_4$ and solvent removed under reduced pressure. The resultant crude product was washed with ethyl acetate (35 ml) to give the title compound (0.81 g, 25%) as a white powder.

$^1H$ NMR ($CDCl_3$) δ: 7.37–7.41 (m, 4H), 7.18–7.29 (m, 6H), 7.15 (t, 1H, J=1 Hz), 4.75 (s, 2H), 2.6 (br, 1H).

c. 4-Methoxy-4-[3-[4-(2-phenylimidazol-1-yl)benzyloxy]phenyl]-3,4,5,6-tetrahydro-2H-pyran The title compound was prepared in a manner similar to that described for 4-methoxy-4-[3-[4-(2-methylimidazol-1-yl)benzyloxy]phenyl]-3,4,5,6-tetrahydro-2H-pyran. (Example 2)

m.p.: 117°–117.5° C.

IR (KBr) $cm^{-1}$: 1519, 1468, 1418, 1310, 1249, 1070, 706.

$^1H$ NMR ($CDCl_3$) δ:7.49 (d, 2H, J=9 Hz), 7.38–7.42 (m, 2H), 7.32 (t, 1H, J=8 Hz), 7.23–7.30 (m, 6H), 7.16 (d, 1H, J=1 Hz), 7.00–7.05 (m, 2H), 6.91 (dd, 1H, J=9, 2 Hz), 5.12 (s, 2H), 3.82–3.91 (m, 4H), 2.98 (s, 3H), 1.92–2.09 (m, 4H).

EXAMPLE 5

4-Methoxy-4-[3-[4-(4-phenylimidazol-1-yl)benzyloxy]phenyl]-3,4,5,6-tetrahydro-2H-pyran The title compound was prepared from 4-phenylimidazole and 4-fluorobenzaldehyde according to the general procedure described for 4-methoxy-4-[3-[4-(2-methylimidazol-1-yl)benzyloxy]phenyl]-3,4,5,6-tetrahydro-2H-pyran (Example 2).

m.p.: 98°–100.5° C.

IR (KBr) $cm^{-1}$: 1526, 1487, 1256, 1072.

$^1H$ NMR ($CDCl_3$) δ: 7.91 (d, 1H, J=1 Hz), 7.85 (dd, 2H, J=7, 1 Hz), 7.60 (d, 2H, J=8 Hz), 7.58 (s, 1H), 7.28–7.50 (m, 6H), 7.06 (d, 1H, J=2 Hz), 7.02 (d, 1H, J=8 Hz), 6.92 (dd, 1H, J=8, 2 Hz), 5.14 (s, 2H), 3.83–3.87 (m, 4H), 2.99 (s, 3H), 1.92–2.09 (m, 4H).

EXAMPLE 6

4-[5-Fluoro-3-[4-(2-methylimidazol-1-yl)benzyloxy]phenyl]-4-methoxy-3,4,5,6-tetrahydro-2H-pyran The title compound was prepared in a manner similar to Example 2, Part b, but using 4-(5-fluoro-3-hydroxyphenyl)-4-methoxy-3,4,5,6-tetrahydro-2H-pyran as starting material.

m.p.: 168°–168.5° C.

IR (KBr) $cm^{-1}$: 1590, 1520, 1416, 1138, 1072.

$^1H$ NMR ($CDCl_3$) δ: 7.56 (d, 2H, J=8 Hz), 7.34 (d, 2H, J=8 Hz), 7.04 (d, 1H, J=1 Hz), 7.01 (d, 1H, J=1 Hz), 6.83 (br s, 1H), 6.75 (ddd, 1H, J=10, 2, 2 Hz), 6.64 (ddd, 1H, J=10, 2, 2 Hz), 5.11 (s, 2H), 3.81–3.86 (m, 4H), 2.99 (s, 3H), 2.38 (s, 3H), 1.88–1.99 (m, 4H).

EXAMPLE 7

4-[3-[2-Fluoro-4(2-methylimidazol-1-yl)benzyloxy]phenyl]-4-methoxy-3,4,5,6-tetrahydro-2H-pyran The title compound was prepared in a manner similar to Example 2 using ethyl 2,4-difluorobenzoate and 2-methylimidazole as starting materials.

m.p.: 121°–122° C.

IR (KBr) $cm^{-1}$: 1585, 1515, 1299, 1249, 1073, 900.

$^1H$ NMR ($CDCl_3$) δ: 7.67 (dd, 1H, J=8, 8 Hz), 7.34 (dd, 1H, J=8, 8 Hz), 7.15 (dd, 1H, J=8, 2 Hz), 7.01–7.11 (m, 5H), 6.94 (dd, 1H, J=8, 3 Hz), 5.19 (s, 2H), 3.83–3.91 (m, 4H), 2.99 (s, 3H), 2.40 (s, 3H), 1.92–2.10 (m, 4H).

The compounds of Examples 8 to 24 were prepared in analogous fashion to Examples 1 to 7, using the appropriate starting materials. In some instances, the product was converted into the hydrochloride salt after isolation.

EXAMPLE 8

4-Methoxy-4-[3-[4-(2-benzylimidazol-1-yl)benzyloxy]phenyl]-3,4,5,6-tetrahydro-2H-pyran m.p.: oil IR (KBr) $cm^{-1}$: 2955, 1606, 1586, 1519, 1485, 1437, 1306, 1260, 1079.

$^1H$ NMR ($CDCl_3$) δ:7.74–6.85 (m, 15H), 5.12 (s, 2H), 4.03 (s, 2H), 3.94–3.76 (m, 4H), 2.98 (s, 3H), 2.10–1.89 (m, 4H).

EXAMPLE 9

4-[3[4-(2-Ethylimidazol-1-yl)benzyloxy]phenyl]-4-methoxy-3,4,5,6-tetrahydro-2H-pyran m.p.: oil IR (neat) $cm^{-1}$: 1519, 1429, 1306, 1255, 1073.

$^1H$ NMR ($CDCl_3$) δ:7.57 (d, 2H, J=8 Hz), 7.33 (dd, 1H, J=8, 8 Hz), 7.32 (d, 2H, J=8 Hz), 7.07 (d, 1H, J=1 Hz), 7.06

(d, 1H, J=3 Hz), 7.02 (d, 1H, J=8 Hz), 6.98 (d, 1H, J=1 Hz), 6.93 (ddd, 1H, J=8, 3, 1 Hz), 5.14 (s, 2H), 3.82–3.88 (m, 4H), 2.98 (s, 3H), 2.67 (q, 2H, J=8 Hz), 1.92–2.09 (m, 4H), 1.26 (t, 3H, J=8 Hz).

EXAMPLE 10

4-Methoxy-4-[3-[3-methyl-4-(2-methylimidazol-1-yl) benzyloxy]phenyl]-3,4,5,6-tetrahydro-2H-pyran m.p.: 121.5°–122° C.

IR (neat) cm$^{-1}$: 1584, 1305, 1251, 1072.

$^1$H NMR (CDCl$_3$) δ:7.44 (s, 1H), 7.38 (d, 1H, J=8 Hz), 7.33 (dd, 1H, J=8, 8 Hz), 7.21 (d, 1H, J=8 Hz), 7.06–7.07 (m, 2H), 7.02 (d, 1H, J=8 Hz), 6.93 (dd, 1H, J=8, 2 Hz), 6.86 (d, 1H, J=1 Hz), 5.10 (s, 2H), 3.82–3.88 (m, 4H), 2.99 (s, 3H), 2.19 (s, 3H), 2.08 (s, 3H), 1.97–2.04 (m, 4H).

EXAMPLE 11

4-Methoxy-4-[3-[4-[2-(pyridin-2-yl)imidazol-1-yl) benzyloxy]phenyl]-3,4,5,6-tetrahydro-2H-pyran m.p.: 103°–105° C.

IR (neat) cm$^{-1}$: 3360, 1598, 1515, 1455, 1267.

$^1$H NMR (CDCl$_3$) δ:8.32 (d, 1H, J=4 Hz), 7.92 (d, 1H, J=8 Hz), 7.70 (dd, 1H, J=1.8, 8 Hz), 7.47 (d, 2H, J=8.4 Hz), 7.39–7.24 (m, 4H), 7.21–7.11 (m, 2H), 7.08–6.98 (m, 2H), 6.96–6.87 (m, 1H), 5.12 (s, 2H), 3.94–3.77 (m, 4H), 2.98 (s, 3H), 2.10–1.90 (m, 4H).

EXAMPLE 12

4-[3-[3-Fluoro-4-(2-methylimidazol-1-yl)benzyloxy] phenyl]-4-methoxy-3,4,5,6-tetrahydro-2H-pyran

MW 396.46 mp: 101.5°–102° C.

IR (KBr): 1584, 1524, 1434, 1304, 1351, 1073 cm$^{-1}$ $^1$H NMR (CDCl$_3$) δ: 7.41–7.29 (m, 4H), 7.07 (d, J=1 Hz, 1H), 7.05–7.02 (m, 2H), 6.96 (br, 1H), 6.91 (dd, J=7, 3 Hz, 1H), 5.13 (s, 2H), 3.91–3.82 (m, 4H), 2.99 (s, 3H), 2.31 (s, 3H), 2.1–1.9 (m, 4H).

EXAMPLE 13

4-[5-Fluoro-3-[2-fluoro-4-(2-methylimidazol-1-yl) benzyloxy]phenyl]-4-methoxy-3,4,5,6-tetrahydro-2H-pyran

MW: 414.46 mp: 133.5°–134° C.

IR (KBr) : 1622, 1593, 1515, 1139, 1072, 1039 cm$^{-1}$ $^1$H NMR(CDCl$_3$) δ: 7.64 (dd, J=8, 8 Hz, 1H), 7.15 (dd,J=8, 2 Hz, 1H), 7.10 (dd, J=10, 2 Hz, 1H), 7.05 (d, J=2 Hz, 1H) 7.01 (d, J=2 Hz, 1H), 6.85 (br, 1H), 6.76 (d, J=10 Hz, 1H, ), 6.65 (ddd, J=10, 2, 2 Hz, 1H), 5.16 (s, 2H), 3.9–3.8 (m, 4H), 3.00 (s, 3H), 2.40 (s, 3H), 2.1–1.8 (m, 4H).

EXAMPLE 14

4-[3-[4-Fluoro-2-(2-methylimidazol-1-yl)benzyloxy] phenyl]-4-methoxy-3,4,5,6-tetrahydro-2H-pyran

MW: 396.46 mp: oil

IR (neat): 1612, 1603, 1508, 1253, 1217, 1073 cm$^{-1}$ $^1$H NMR (CDCl$_3$) δ: 7.69 (dd, J=9, 4 Hz, 1H), 7.3–7.2 (m, 2H), 7.1–6.9 (m, 4H), 6.88 (t, J=2 Hz, 1H), 6.73 (dd, J=8, 2 Hz, 1H), 4.70 (s, 2H), 3.9–3.8 (m, 4H), 2.95 (s, 3H), 2.25 (s, 3H), 2.1–1.8 (m, 4H).

EXAMPLE 15

4-[3-[2-Chloro-4-(2-methylimidazol-1-yl)benzyloxy]-5-fluorophenyl]-4-methoxy-3,4,5,6-tetrahydro-2H-pyran hydrochloride

MW: 467.37 mp: 204°–205° C.

IR (KBr): 1613, 1602, 1441, 1303, 1146, 1039 cm$^{-1}$ $^1$H NMR (CDCl$_3$) δ: 7.89 (d, J=8 Hz, 1H), 7.51 (br, 1H), 7.45 (d, J=1 Hz, 1H), 7.40 (d, J=8 Hz, 1H), 7.20 (d, J=1 Hz, 1H), 6.87 (br, 1H), 6.79 (ddd, J=10, 2, 2 Hz, 1H), 6.65 (ddd, J=10, 2, 2 Hz, 1H), 5.22 (s, 2H), 3.9–3.8 (m, 4H), 3.02 (s, 3H), 2.80 (s, 3H), 2.0–1.8 (m, 4H).

EXAMPLE 16

4-[3-[2-Chloro-4-(2-methylimidazol-1-yl)benzyloxy] phenyl]-4-methoxy-3,4,5,6-tetrahydro-2H-pyran hydrochloride

MW: 449.38 mp: 224°–225° C.

IR (KBr) : 1606, 1305, 1243, 1066, 1046, 1038, 755 cm$^{-1}$ $^1$H NMR(CDCl$_3$) δ:7.93 (d, J=8 Hz, 1H), 7.48 (d, J=2 Hz, 1H), 7.45 (d, J=2 Hz, 1H), 7.4–7.3 (m, 2H), 7.19 (d, J=2 Hz, 1H), 7.1–7.0 (M, 2H), 6.94 (dd, J=8.2 Hz, 1H), 5.25 (s, 2H), 3.9–3.8 (m, 4H), 3.01 (s, 3H), 2.79 (s, 3H), 2.1–1.9 (m,4H).

EXAMPLE 17

4-[5-Fluoro-3-[2-methyl-4-(2-methylimidazol-1-yl) benzyloxy]phenyl]-4-methoxy-3,4,5,6-tetrahydro-2H-pyran hydrochloride

MW: 446.95 mp: 207°–208° C.

IR (KBr): 1624, 1591, 1528, 1439, 1151, 1073 cm$^{-1}$ $^1$H NMR (CDCl$_3$) 3: 7.70 (d, J=9 Hz, 1H), 7.42 (d, J=2 Hz, 1H), 7.3–7.2 (m, 2H), 7.17 (d, J=2 Hz, 1H), 6.85 (br, 1H), 6.87 (ddd, J=9, 2, 2 Hz, 1H), 6.65 (ddd, J=10,2,2 Hz, 1H), 5.10 (s, 2H), 3.9–3.8 (m, 4H), 3.02 (s,3H), 2.76 (s, 3H), 2.49 (s, 3H), 2.0–1.8 (m, 4H).

EXAMPLE 18

4-[5-Fluoro-3-[4-(2-methylimidazol-1-yl)-2-trifluoromethylbenzyloxy]phenyl]-4-methoxy-3,4,5,6-tetrahydro-2H-pyran hydrochloride

MW: 500.92 mp: 198.5°–199.5° C.

IR (KBr): 1595, 1314, 1176, 1141, 1125, 1062 cm$^{-1}$ $^1$H NMR(CDCl$_3$)δ8:11 (d,J=9 Hz, 1H), 7.78(br, 2H),7.48 (d,J=2 Hz, 1H),7.24 (d, J=2 Hz, 1H), 6.85 (br, 1H), 6.80 (d, J=10 Hz, 1H), 6.61 (ddd, J=10, 2, 2 Hz, 1H), 5.34 (s, 2H), 3.9–3.8 (m, 4H), 3.01 (s, 3H), 2.81 (s, 3H), 2.0–1.8 (m,4H).

EXAMPLE 19

4-Methoxy-4-[3-[4-(2-methylimidazol-1-yl)-2-trifluoromethylbenzyloxy]phenyl]-3,4,5,6-tetrahydro-2H-pyran hydrochloride

MW: 482.93 mp: 213°–215° C.

IR (KBr): 1442, 1315, 1172, 1123, 1065, 1054 cm$^{-1}$ $^1$H NMR (CDCl$_3$) δ: 8.15 (d, J=8 Hz, 1H), 7.8–7.6 (m, 2H), 7.48 (d, J=2 Hz, 1H), 7.35(dd,J=8.8 Hz, 1H),7.23(d,J=2 Hz, 1H),7.1–7.0(m,2H),6.90(dd,J=7.3 Hz, 1H), 5.37 (s, 2H), 3.9–3.8 (m, 4H), 3.00 (s, 3H), 2.80 (s, 3H), 2.1–1.9 (m,4H).

EXAMPLE 20

4-[2,4-Difluoro-3-[4-(2-methylimidazol-1-yl)benzyloxy] phenyl]-4-methoxy-3,4,5,6-tetrahydro-2H-pyran hydrochloride

MW: 450.92 mp: 174.5°–175.5° C.

IR (KBr): 1606, 1498, 1455, 1444, 1281, 1094, 1023, 818 cm$^{-1}$ $^1$H NMR(CDCl$_3$) δ:7.75 (d, J=8 Hz, 2H), 7.5–7.4 (m, 3H), 7.20 (d, J=2 Hz, 1H), 7.09–6.91 (m, 2H), 5.25 (s, 2H), 3.9–3.8 (m, 4H), 3.05 (s, 3H), 2.76 (s, 3H), 2.2–2.1 (m, 4H).

EXAMPLE 21

4-[5-Fluoro-3-[2-methoxy-4-(2-methylimidazol-1-yl) benzyloxy]phenyl]-4-methoxy-3,4,5,6-tetrahydro-2H-pyran hydrochloride

MW: 462.95 mp: 197.5°–198.5° C.

IR (KBr) :1612, 1590, 1440, 1329, 1242, 1150, 1042 cm$^{-1}$ $^1$H NMR (CDCl$_3$) δ:7.70 (d, J=7 Hz, 1H), 7.42 (br, 1H), 7.21 (d, J=2 Hz, 1H), 7.1–6.9 (m, 2H), 6.86 (br, 1H), 6.75 (d, J=9 Hz, 1H), 6.64 (d, J=10 Hz, 1H), 5.14 (s, 2H), 3.97 (s, 3H), 3.9–3.8 (m, 4H), 3.01 (s, 3H), 2.79 (s, 3H), 1.9–2.0 (m, 4H).

EXAMPLE 22

4-[3-[4-(2-Ethylimidazol-1-yl)benzyloxy]-5-fluorophenyl]-4-methoxy-3,4,5,6-tetrahydro-2H-pyran hydrochloride

MW: 446.95 mp: 210°–211° C.

IR (KBr): 1624, 1596, 1523, 1148, 1073, 1038 cm$^{-1}$ $^1$H NMR(CDCl$_3$) δ:7.71 (d, J=8 Hz, 2H), 7.47 (d, J=2 Hz, 1H), 7.42 (d, J=8 Hz, 2H), 7.15 (d, J=2 Hz, 1H), 6.85 (br, 1H), 6.77 (ddd, J=10, 2, 2 Hz, 1H), 6.63 (ddd, J=10, 2, 2 Hz, 1H), 5.17 (s, 2H), 3.9–3.8 (mn, 4H), 3.06 (q, J=8 Hz, 2H), 3.01 (s, 3H), 2.0–1.9 (m, 4H), 1.41 (t, J=8 Hz, 3H).

EXAMPLE 23

4-[2,5-Difluoro-3-[4-(2-methylimidazol-1-yl)benzyloxy] phenyl]-4-methoxy-3,4,5,6-tetrahydro-2H-pyran hydrochloride

MW: 450.92 mp: 228°–231° C. (dec.)

IR (KBr): 1527, 1484, 1335, 1103, 853, 771 cm$^{-1}$ $^1$H NMR (CDCl$_3$) δ:7.73 (d, J=8 Hz, 2H), 7.43 (d, J=8 Hz, 2H), 7.43 (d, J=2 Hz, 1H), 7.19 (d, J=2 Hz, 1H), 6.8–6.7 (m, 2H), 5.20 (s, 2H), 3.9–3.8 (m, 4H), 312 (s, 3H), 2.77 (s, 3H), 2.3–2.0 (m, 4H).

EXAMPLE 24

4-[6-Fluoro-2-[4-(2-methylimidazol-1-yl)benzyloxy] phenyl]-4-methoxy-3,4,5,6-tetrahydro-2H-pyran

MW: 396.46 mp: 149°–150.5° C.

IR (KBr): 1606, 1518, 1454, 1418, 1304, 1282, 1071 cm$^{-1}$ $^1$H NMR (CDCl$_3$) δ:7.62 (d, J=9 Hz, 2H), 7.33 (d, J=8 Hz, 2H), 7.23 (ddd, J=8, 8, 6 Hz, 1H), 7.04 (d, J=2 Hz, 1H), 7.02 (d, J=2 Hz, 1H), 6.79 (d, J=8 Hz, 1H), 6.73 (ddd, J=13, 8 Hz, 1H), 5.17 (s, 2H), 4.0–3.9 (m, 2H), 3.8–3.7 (m, 2H), 3.12 (s,3H), 2.5–2.4 (m, 2H), 2.39 (s, 3H), 2.4–2.3 (m, 2H).

EXAMPLE 25

4-[5-Fluoro-3-[4-(2-methylimidazol-1-yl)benzyloxy] phenyl]-4-methoxy-3,4,5,6-tetrahydro-2H-pyran 4-(5-Fluoro-3-hydroxyphenyl)-4-methoxy-3,4,5,6-tetrahydro-2H-pyran was obtained as described in EP 0 385 662 A2, as a white solid.

mp: 130°–132° C.

$^1$H NMR (CDCl$_3$) δ:6.70–6.61 (m, 2H), 6.50 (dt, J=10 and 2 Hz, 1H), 6.30 (s, 1H), 3.88–3.84 (m, 4H), 3.02 (s, 3H), 2.05–1.90 (m, 4H).

IR (KBr): 3250, 1620, 1610, 1440, 1320, 1130 cm$^{-1}$

Elemental Anal: C$_{12}$H$_{15}$FO$_3$

Calc. C 63.70; H 6.70%

Found C 63.72; H 6.83% a. Ethyl 4-(2-methylimidazol-1-yl)benzoate

A mixture of 2-methylimidazole (50 g, 0.6 mol), ethyl 4-fluorobenzoate (100 g, 0.6 mol) and potassium carbonate (415 g, 3 mol) in dry DMSO (1.5 l) was heated at 120° C. for 66 hours under a nitrogen atmosphere. After cooling to room temperature, the reaction mixture was poured into ice-cold water (1 l), and extracted with Et$_2$O (750 ml×2). The organic phase was washed with water (500 ml) and brine (500 ml), dried (MgSO$_4$) and evaporated. The residual solid was recrystallized from ethyl acetate-hexane to give ethyl 4-(2-methylimidazol-1-yl)benzoate (47 g, 33%) as yellow needles.

mp: 72°–73° C.

$^1$H NMR (CDCl$_3$) δ: 8.22–8.12 (m, 2H), 7.43–7.33 (m, 2H), 7.10–6.99 (m, 2H), 4.42 (q, J=7 Hz, 2H), 2.42 (s, 3H), 1.43 (t, J=7 Hz, 3H).

IR (KBr): 1720, 1610, 1520, 1420, 1280 cm$^{-1}$

Elemental Anal: C$_{13}$H$_{14}$N$_2$O$_2$

Calc. C 67.80; H 6.10; N 12.20%

Found C 67.97; H 6.17; N 12.20% b. 4-(2-Methylimidazol-1-yl)benzyl alcohol

To a solution of ethyl 4-(2-methylimidazol-1-yl)benzoate (46 g, 0.2 mol) in dry CH$_2$Cl$_2$ (1 l) cooled to –75° C. under a nitrogen atmosphere was added diisobutyl-aluminum hydride (540 ml, 0.93M in hexane) carefully over 30 minutes and then the mixture allowed to warm slowly to ambient temperature. After stirring for 5 hours the reaction mixture was cooled in an ice-bath and methanol (30 ml) carefully added. A 30% aqueous solution of Rochelle's salt (500 ml) was then added and the mixture stirred at ambient temperature for 16 hours. Insolubles (essentially product) were removed by filtration and the organic phase separated and washed with water (500 ml), dried (MgSO$_4$) and evaporated. The combined resultant solids were recrystallized from ethanol (ca 300 ml) to afford 4-(2-methylimnidazol-1-yl) benzyl alcohol (35.6 g, 95%) as white needles.

mp: 167°–168° C.

$^1$H NMR (DMSO-d$_6$) δ: 7.50–7.33 (m, 4H), 7.25 (d, J=1.5 Hz, 1H), 6.90 (d, J=1.1 Hz, 1H), 5.33 (t, J=6 Hz, 1H), 4.56 (d, J=6 Hz, 2H), 2.27 (s, 3H).

IR (KBr) : 3200, 1520, 1420, 1520, 1310, 1060 cm$^{-1}$

Elemental Anal: C$_{11}$H$_{12}$N$_2$O

Calc. C 70.20; H 6.40; N 14.90%

Found C 70.12; H 6.41; N 14.81% c. 4-(2-Methylimidazol-1-yl)benzyl chloride hydrochloride 4-(2-Methylimidazol-1-yl)benzyl alcohol (1.28 g, 6.8 mmol) in SOCl$_2$ (5 ml) was stirred at ambient temperature for 30 minutes and then volatiles removed under reduced pressure. The resultant crude product was washed with minimal dry Et$_2$O and dried in vacuo to afford 4-(2-methylimidazol-1-yl)benzyl chloride hydrochloride (1.65 g, quant.) as white solids.

for free base:

$^1$H NMR (CDCl$_3$) δ:7.56–7.47 (m, 2H), 7.34–7.25 (m, 2H), 7.03 (s, 1H), 7.00 (s, 1H), 4.65 (s, 2H), 2.37 (s, 3H). d. 4-[5-Fluoro-3-[4-(2-methylimidazol-1-yl)benizyloxy] phenyl]-4-methoxy-3,4,5,6-tetrahydro-2H-pyran A mixture of 4-(5-fluoro-3-hydroxyphenyl)-4-methoxy-3, 4,5,6-tetrahydro-2H-pyran (1.4 g, 6.8 mmol), 4-(2-methylimidazol-1-yl)benzyl chloride hydrochloride (1.65 g, 6.8mmol) and potassium carbonate (7.2 g, 68 mmol) in dry DMF (10 ml) was stirred at 120° C. for 2 hours. The mixture was poured into water (100 ml) and extracted with ethyl acetate - benzene (300 ml, 2:1 v/v). The organic phase was washed with water (100 ml), brine (100 ml), dried (MgSO$_4$) and evaporated. Purification of the residual yellow solids by column chromatograghy on silica gel (100 g) eluting with CH$_2$Cl$_2$/methanol=10:1 and recrystallization from ethyl acetate-hexane gave 4-[5-fluoro-3-[4-(2-methylimidazol-1-yl)benzyloxy]phenyl]-4-methoxy-3,4,5,6-tetrahydro-2H-pyran (1.0 g, 39%) as off-white solids.

mp: 168°–168.5° C.

¹H NMR (CDCl₃) δ:7.56 (d, J=8 Hz, 2H), 7.34 (d, J=8 Hz, 2H), 7.04 (d, J=1 Hz, 1H), 7.01 (d, J=1 Hz, 1H), 6.83 (br. s, 1H), 6.75 (ddd, J=10, 2 and 2 Hz, 1), 6.64 (ddd, J=10, 2 and 2 Hz, 1H), 5.11 (s, 2H), 3.86–3.81 (m, 4H), 2.99 (s, 3H), 2.38 (s, 3H), 1.99–1.88 (m, 4H).

IR (KBr): 1590, 1520, 1416, 1138, 1072 cm⁻¹

Elemental Anal: $C_{23}H_{25}FN_2O_3$

Calc. C 69.68; H 6.36; N 7.07; F 4.79%

Found C 69.62; H 6.39; N 7.02; F 4.62%

The compounds of Examples 26 to 40 were prepared from appropriate imidazolylbenzyl chlorides and phenols according to the general procedure of Example 25, Part d. In some instances, the product was further converted into its hydrochloride salt.

EXAMPLE 26

4-[5-Fluoro-3-[4-(2-isopropylimidazol-1-yl)benzyloxy]phenyl]-4-methoxy-3,4,5,6-tetrahydro-2H-pyran hydrochloride

MW: 460.97 mp: 140°–143° C.

IR (KBr): 1620, 1590, 1520, 1300, 1150 cm⁻¹

¹H NMR(DMSO-d₆) δ:7.86(d, J=2.2 Hz, 1H), 7.83(d, J=2.2 Hz, 1H), 7.74(d, J=8.4 Hz, 2H), 7.68(d, J=8.4 Hz, 2H), 6.95–6.77(m, 3H), 5.28(s, 2H), 3.78–3.59(m, 4H), 3.15–3.00(m, 1H), 2.89(s, 3H), 2.00–1.80(mn, 4H), 1.31(d, J=7.0 Hz, 6H).

EXAMPLE 27

4-[5-Fluoro-3-[4-(2-propylimidazol-1-yl)benzyloxy]phenyl]-4-methoxy-3,4,5,6-tetrahydro-2H-pyran hydrochloride

MW: 460.97 mp: 142°–146° C.

IR (KBr): 1620, 1590, 1530, 1440, 1290, 1140 cm⁻¹

¹H NMR (DMSO-d₆) δ:7.89(d, J=1.8 Hz, 1H), 7.82(d, J=2.2 Hz, 1H), 7.88–7.63(m, 4H), 6.95–6.77(m, 3H), 5.27(s, 2H), 3.77–3.59(m, 4H), 2.89(s, 3H), 2.86(t=7.7 Hz, 2H), 2.00–1.80(m, 4H), 1.70–1.52(m, 2H), 0.79(t, J=7.3, 3H).

EXAMPLE 28

4-[2,3-Difluoro-5-[4-(2-methylimidazol-1-yl)benzyloxy]phenyl]4-methoxy-3,4,5,6-tetrahydro-2H-pyran hydrochloride

MW: 450.92 mp: >200° C.

IR (KBr): 1600, 1520, 1480, 1220, 880 cm⁻¹

¹H NMR(DMSO-d₆) δ:7.90(d, J=1.8 Hz, 1H), 7.79(d, J=1.8 Hz, 1H), 7.77–7.62(m, 4H), 7.26–7.15(m, 1H), 6.84–6.75(m, 1H), 5.24(s, 2H), 3.79–3.60 (m, 4H), 2.98(s, 3H), 2.54(s, 3H), 2.10–1.90(m, 4H).

EXAMPLE 29

4-[2-Fluoro-5-[4-(2-methylimidazol-1-yl)benzyloxy]phenyl]-4-methoxy-3,4,5,6-tetrahydro-2H-pyran hydrochloride

MW: 432.93 mp: >200° C.

IR (KBr): 1600, 1580, 1520, 1480, 1060, 1050, 870 cm⁻¹

¹H NMR(DMSO-d₆) δ: 7.89(d, J=2.2 Hz, 1H), 7.79(d, J=2.2 Hz, 1H), 7.76–7.62(m, 4H), 7.14(dd, J=8.8, 11.7 Hz, 1H), 7.07–6.91 (m, 2H), 5.22(s, 2H), 3.78–3.60(m, 4H) 2.95(s, 3H), 2.55(s, 3H), 2.10–1.90(m, 4H).

EXAMPLE 30

4-[2,6-Difluoro-3-[4-(2-methylimidazol-1-yl)benzyloxy]phenyl]-4-methoxy-3,4,5,6-tetrahydro-2H-pyran

MW: 414.45 mp: oil

IR (film): 2950, 1580, 1480, 1420, 1300, 1250 cm⁻¹

¹H NMR (CDCl₃) δ: 7.57(d, J=8.4 Hz, m, 2H), 7.33(d, J=8.4 Hz, 2H), 7.04(d, J=1.5 Hz, 1H), 7.01(d,J=1.5 Hz, 1H), 6.97(ddd,4.8, 8.8, 8.8 Hz, 1H), 6.88–6.75(m, 1H), 5.13(s, 2H), 4.00–3.70(m, 4H), 3.13(s, 3H), 2.37(s, 3H), 2.40–2.20 (m,4H).

EXAMPLE 31

4-[2-Fluoro3-[4-(2-methylidazol-1-yl) benzyloxy]phenyl]-4-methoxy-3,4,5,6-tetrahydro-2H-pyran

MW: 396.46 mp: oil

IR (film): 1520, 1460, 1420, 1270, 1070 cm⁻¹ ¹H NMR (CDCl₃) δ: 7.62–7.54(m, 2H), 7.38–7.29(m, 2H), 7.12–6.92 (m, 5H), 5.18(s, 2H), 3.98–3.78(m, 4H), 3.09(s, 3H), 2.38(s, 3H), 2.29–2.05(m, 4H).

This product was converted into its p-toluenesulfonate salt in a similar manner to Example 43.

MW: 568.67 mp: 170°–171° C.

IR (KBr): 1620, 1530, 1480, 1280, 1240, 1160 cm⁻¹

¹H NMR (DMSO-d₆) δ:7.91(d, J=2.2 Hz, 1H), 7.81–7.62 (m, 5H), 7.52–7.43(m, 2H), 7.32–7.06(m 4H), 7.01–6.91(m, 1H), 5.28(s, 2H), 3.80–3.61(m, 4H), 2.95 (s, 3), 2.53(s, 3H), 2.28(s, 3H), 2.13–1.90(m, 4H).

EXAMPLE 32

4-Methoxy-4-[4-[3-(2-methylimidazol-1-yl)benzyloxy]phenyl]-3,4,5,6-tetrahydro-2H-pyran

MW: 378.47 mp: 123°–126° C.

IR (KBr): 1610, 1507, 1230, 1183, 1072, 1008 cm⁻¹

¹H NMR (CDCl₃) δ:7.56–7.21 (m, 6H), 7.06–6.93(m, 4H), 5.14(s, 2H), 3.94–3.75 (m, 4H), 2.95(s, 3H), 2.34(s, 3H), 2.10–1.90(m, 4H).

EXAMPLE 33

4-Methoxy-4-[4-[4-(2-methylimidazol-1-l)benzyloxy]phenyl]-3,4,5,6-tetrahydro-2H-pyran

MW: 378.47 mp: 150°–151° C.

IR (KBr): 1610, 1520, 1510, 1420, 1305, 1245, 1210, 1075, 1000 cm⁻¹

¹H NMR (CDCl₃) δ: 7.57(d, J=8.4 Hz, 2H), 7.39–7.28(m, 4H), 7.06–6.95(m, 4H), 5.13(s, 2H), 3.95–3.75(m, 4H), 2.96(s, 3H), 2.38(s, 3H), 2.10–1.90(m, 4H).

EXAMPLE 34

4-[5-Fluoro-3-[3-(2-methylimidazol-1-yl)benzyloxy]phenyl]-4-methoxy-3,4,5,6-tetrahydro-2H-pyran

MW: 396.46 mp: oil

IR (film): 2960, 1595, 1500, 1445, 1305 cm⁻¹

¹H NMR(CDCl₃) δ:7.58–7.44(m, 2H), 7.39(br s, 1H), 7.33–7.21(m, 1H), 7.08–6.98(m, 2H), 6.86–6.56(m, 3H), 5.12(s, 2H), 3.93–3.73(m, 4H), 2.98(s,3H), 2.36 (s, 3H), 2.12–1.85(m, 4H).

EXAMPLE 35

4-[5-Fluoro-3-[4-(2-trifluroethylimidizol-1-yl)benzyloxy]phenyl]-4-methoxy-3,4,5,6-tetrahydro-2H-pyran

MW: 450.44 mp: 96°–98° C.

IR (KBr): 1695, 1440, 1190, 1130 cm⁻¹

¹H NMR (CDCl₃) δ:7.57(d, J=8.8 Hz, 2H), 7.41(d, J=8.4 Hz, 2H), 7.24(d, J=1.5 Hz, 1H), 7.16(d, J=1.1, 1H), 6.85–6.60(m, 3H), 5.14(s, 2H), 3.90–3.80 (m, 4H), 2.98(s, 3H), 2.05–1.85(m, 4H).

EXAMPLE 36

4-Ethoxy-4-[5-fluoro-3-[4-(2-methylimidazol-1-yl) benzyloxy]phenyl]-3,4,5,6-tetrahydro-2H-pyran hydrochloride

MW: 446.95 mp: 195°–197° C.

IR (KBr): 3235, 2905,2870, 1621, 1593,1516, 1417, 1382, 1335, 1299, 1145 cm⁻¹

¹H-NMR (DMSO-d₆) δ: 7.87(d,J=1.8 Hz, 1H), 7.77(d, J=21.8 Hz, 1H), 7.71(d, J=8.4 Hz, 2H), 7.68(d, J=8.4 Hz, 2H), 6.92–6.77(m, 3H), 5.26(s, 2H), 3.70–3.65(m, 4H), 3.02(q, J=7.0 Hz, 2H), 2.56(s, 3H), 1.97–1.81(m, 4H), 1.05(t, J=7.0 Hz, 3H).

EXAMPLE 37

4-[5-Fluoro-3-[4-(2-methylidazol-1-yl)benzyloxy]phenyl]-4-hydroxy-3,4,5,6-tetrahydro-2H-pyran

MW: 382.44 mp: 190°–191° C.

IR (KBr): 3235, 2905, 2870, 1621, 1593, 1516, 1417, 1382, 1335, 1299, 1145 cm⁻¹.

¹H NMR (CDCl₃) δ:7.57–7.53(m, 2H), 7.35–7.31 (m, 2H), 7.02(d, J=1.5 Hz, 1H), 7.01(d, J=1.5 Hz, 1H), 6.96(m, 1H), 6.85(ddd, J=1.5, 2.2, 9.5 Hz, 1H), 6.63(ddd, J=2.2, 2.6, 9.9 Hz, 1H), 5.11(s, 2H), 3.99–3.83(m, 4H), 2.37(s, 3H), 2.21–2.08(m,2H), 1.97(br s, 1H), 1.70–1.61(m, 2H).

EXAMPLE 38

4-[5-Fluoro-3-[4-(2-methylimidazol-1-yl)benzyloxy] phenyl]-4-methylthio-3,4,5,6-tetrahydro-2H-pyran hydrochloride

MW: 448.99 mp: 216.0°–217.0° C.

IR (KBr): 2600, 1620, 1590, 1530, 1430, 1140 cm⁻¹

¹H NMR (DMSO-d₆) δ:7.89 (d, J=2.2 Hz, 1H), 7.78 (d, J=2.2 Hz, 1H), 7.74 (d, J=8.4 Hz, 2H), 7.66 (d, J=8.4 Hz, 2H), 6.89 (s, 2H), 6.85 (d, J=1.8 Hz 1H), 5.26 (s, 2H), 3.85–3.75 (m, 2H), 3.62–3.53 (m, 2H), 2.54 (s, 3H), 2.14–2.05(m, 4H), 1.63 (s, 3H).

EXAMPLE 39

4-[5-Fluoro-3-[4-(2-methylimidazol-1-yl)benzyloxy] phenyl]-4-methylsulfinyl-3,4,5,6-tetrahydro2H-pyran hydrochloride

MW: 464.99 mp: 175.1°–175.9° C.

IR (KBr): 2600, 1620, 1600, 1590, 1530, 1150, 1055, 1030, 990 cm⁻¹

¹H NMR (DMSO-d₆) δ:7.89 (d, J=1.8 Hz, 1H), 7.78 (s, 1H), 7.74 (d, J=8.2 Hz, 2H), 7.67 (d, J=8.2 Hz, 2H), 7.02 (d, J=11.0 Hz, 1H), 6.95–6.87 (m, 2H), 5.29 (s, 2H), 3.92 (d, J=11.6 Hz, 1H), 3.80 (d, J=11.6 Hz, 1H), 3.40–3.18 (m, 2H), 2.55 (s, 3H), 2.38–2.20 (m, 2H), 2.19–1.96 (m, 2H), 1.91 (s, 3H).

EXAMPLE 40

4-[5-Fluoro-3-[4-(2-methylimidazol-1-yl)benzyloxy] phenyl]-4-methylsulfonyl-3,4,5,6-tetrahydro-2H-pyran hydrochloride

MW: 480.99 mp: 230.1°–230.9° C.

IR (KBr): 2850, 1625, 1590, 1530, 1330, 1300, 1290, 1270, 1140, 1130, 1100 cm⁻¹

¹H NMR (DMSO-d₆) δ:7.87 (d, J=2.2 Hz, 1H), 7.78 (d, J=2.2 Hz, 1H), 7.75 (d, J=8.4 Hz, 2H), 7.65 (d, J=8.4 Hz, 2H), 7.11 (s, 1H), 7.07 (s, 2H), 5.29 (s, 2H), 3.89–3.82 (m, 2H), 3.18–3.02 (m, 2H), 2.67 (s, 3H), 2.62–2.48 (m, 2H), 2.54 (s, 3H), 2.29–2.14 (m, 2H).

EXAMPLE 41

4-[5-Fluoro-3-[4-(2-methylimidazol-1-yl)benzyloxy] phenyl]-4-methoxy-3,4,5,6-tetrahydro-2H-pyran hydrochloride To a solution of 4-[5-fluoro-3-[4-(2-methylimidazol-1-yl) benzyloxy]phenyl]-4-methoxy-3,4,5,6-tetrahydro-2H-pyran (0.5 g, 1.3 mmol) in dry CH₂Cl₂ (5 ml) was added "Hydrogen Chloride; Methanol Reagent 10" (4 ml, Tokyo Chemical Industries) at ambient temperature. After stirring for 10 minutes solvent was removed under reduced pressure. The crude product was recrystallized from isopropyl alcohol (4 ml) -ethanol (3 ml) to give 4-[5-fluoro-3-[4-(2-methylimidazol-1-yl) benzyloxy]phenyl]-4-methoxy-3,4,5, 6-tetrahydro-2H-pyran hydrochloride (0.3 g, 55%) as white solids.

mp: 233°–234° C. (dec.)

¹H NMR (CDCl₃) δ:7.71 (d, J=8 Hz, 2H), 7.43 (d, J=2 Hz, 1H), 7.42 (d, J=8 Hz, 2H), 7.19 (d, J=2 Hz, 1H), 6.84 (br. s, 1H), 6.77 (ddd, J=10, 2 and 2 Hz, 1H), 6.62 (ddd, J=10, 2 and 2 Hz, 1H), 5.16 (s, 2H), 3.9–3.8 (m, 4H), 3.00 (s, 3H), 2.77 (s, 3H), 2.0–1.8 (m, 4H).

IR (KBr): 1625, 1590, 1528, 1327, 1147 cm⁻¹

Elemental Anal: C₂₃H₂₅FN₂O₃ HCl

Calc. C 63.81; H 6.05; N 6.47; Cl 8.19; F 4.39%

Found C 63.63; H 6.17; N 6.42; Cl 8.18; F 4.32%

EXAMPLE 42

4-[5-Fluoro-3-[4-(2-methylimidizol-1-yl)benzyloxy] phenyl]-4-methoxy-3,4,5,6-tetrahydro-2H-pyran fumarate To a solution of 4-[5-fluoro-3-[4-(2-methylimidazol-1-yl) benzyloxy]phenyl]-4-methoxy-3,4,5,6-tetrahydro-2H-pyran (150 mg, 0.38 mmol) in MeOH (3 ml) was added fumaric acid (44 mg, 0.38 mmol). The resulting solution was concentrated in vacuo. The residual solid was recrystallized from ethanol to afford 152 mg (77%) of 4-[5-fluoro-3-[4-(2-methylimidazol-1-yl)benzyloxy]phenyl]-4-methoxy-3,4, 5,6-tetrahydro-2H-pyran fumarate as a white powder.

mp: 154°–155° C.

IR (KBr): 1626, 1595, 1529, 1392, 1290, 1144, 1075 cm⁻¹

¹H NMR (DMSO-d₆) δ:7.62 (br d, J=8.4 Hz, 2H), 7.49 (br d, J=8.4 Hz, 2H), 7.31 (d, J=1.1 Hz, 1H), 7.00–6.74 (M, 4H), 6.62(s, 2H), 5.21 (s, 2H), 3.80–3.58(m, 4H), 2.89 (s, 3H), 2.30 (s, 3H), 2.00–1.80 (m, 4H).

EXAMPLE 43

4-[5-Fluoro-3-[4-(2-methylimidazol-1-yl)benzyloxy] phenyl]-4-methoxy-3,4,5,6-tetrahydro-2H-pyran p-toluenesulfonate 4-[5-Fluoro-3-[4-(2-methylimidazol-1-yl)benzyloxy] phenyl]-4-methoxy-3,4,5,6-tetrahydro-2H-pyran p-toluenesulfonate was prepared in a similar manner to Example 42, employing p-toluenesulfonic acid instead of fumaric acid.

mp: 168°–171° C.

IR(KBr): 1625, 1595, 1530, 1220, 1190cm⁻¹

¹H NMR (DMSO-d₆) δ:7.90 (d, J=2.2 Hz, 1H), 7.78 (d, J=2.2 Hz, 1H), 7.74 (br d, J=8.4 Hz, 2H), 7.66 (br d, J=8.4 Hz, 2H), 7.47 (br d, J=8.2 Hz, 2H), 7.11 (br d, J=7.7 Hz, 2H), 6.95–6.75 (m, 3H), 5.26 (s, 2H), 3.80–3.60 (m, 4H), 2.89 (s, 3H), 2.52 (s, 3H), 2.28 (s, 3H), 2.00–1.80 (m, 4H).

EXAMPLE 44

4-[5-Fluoro-3-[4-(2-methylimidazol-1-yl)benzyloxy]phenyl]-4-methoxy-3,4,5,6-tetrahydro-2H-pyran L-tartrate 4-[5-Fluoro-3-[4-(2-methylimidazol-1-yl)benzyloxy)phenyl]-4-methoxy-3,4,5,6-tetrahydro-2H-pyran L-tartrate was prepared in a similar manner to Example 42, employing L-tartrate instead of fumaric acid.

mp: 167°–171° C.

IR (KBr) : 1614, 1528, 1439, 1300, 1075 cm$^{-1}$ $^1$H NMR (DMSO-d$_6$) δ:7.62 (br d, J=8.4 Hz, 2H), 7.49 (br d, J=8.4 Hz, 2H), 7.32 (br s, 1H), 7.08–6.73 (m, 4H), 5.21 (s, 2H), 4.28 (s, 2H), 3.78–3.55 (m, 4H), 3.40 (br, 2H), 2.89 (s, 3H), 2.29 (s, 3H), 2.00–1.78 (m, 4H).

EXAMPLE 45

4-Methoxy-4-[3-[4-(2-methylimidazol-1-yl)benzyl]thio]phenyl]-3,4,5,6-tetrahydro-2H-pyran mp: 95.5°–96° C.

IR (KBr): 1518, 1421, 1303, 1070, 762 cm$^{-1}$ $^1$H NMR (CDCl$_3$) δ:7.38 (d, J=8 Hz, 2H), 7.33–7.23 (m, 4H), 7.20 (d, J=8 Hz 2H), 7.02 (d, J=1 Hz, 1H), 6.97 (d, J=1 Hz, 1H), 4.16 (s, 2H), 3.85–3.79 (m, 4H), 2.93 (s, 3H), 2.34 (s, 3H), 1.95–1.90 (m, 4H).

EXAMPLE 46

4-Methoxy-4-(hydroxyphenyl)-3,4,5,6-tetrahydro-2H-pyran compounds listed below were prepared from the appropriate phenols, using standard methods, according to the following reaction sequence:

(i) protection of the phenolic hydroxy group as its t-butyldimethylsilyl ether;

(ii) lithiation with sec-butyllithium or n-butyllithium at –78° C.;

(iii) condensation with tetrahydro-4H-pyran-4-one;

(iv) methylation of the tertiary hydroxy group thus formed using sodium hydride or n-butyllithium/methyl iodide; and (v) removal of the silyl protecting group using tetrabutylammonium fluoride.

1. 4(2,4-Difluoro-3-hydroxyphenyl)-4-methoxy-3,4,5,6-tetrahydro2H-pyran

Prepared from 2,6-difluorophenol.

MW: 244.26

$^1$H NMR (CDCl$_3$) δ:6.7–6.9 (m, 2H), 3.8–4.0 (m, 4H), 3.06 (s, 3H), 2.0–2.2(m,4H).

2. 4-(2-Fluoro-3-hydroxyphenyl)-4-methoxy-3,4,5,6-tetrahydro-2H-pyran

Prepared from 2-difluorophenol.

MW: 226.27

$^1$H NMR (CDCl$_3$) δ:7.07–6.92(m, 2H), 6.88–6.79(m, 1H), 5.71(d, J=5.5 Hz, 1H), 4.00–3.78(m, 4H), 3.08(s, 3H), 2.27–2.02(m, 4H).

3. 4-(2-Fluoro-5-hydroxyphenyl)-4-methoxy-3,4,5,6-tetrahydro-2H-pyran

Prepared from 4-fluorophenol.

MW: 226.27

$^1$H NMR (CDCl$_3$) δ:6.92(dd, J=8.4, 11.7 Hz, 1H), 6.81 (dd, J=2.9, 6.2 Hz, 1H), 6.72(ddd, J=3.3, 3.3; 8.4 Hz, 1H), 5.58(br s, 1H), 3.99–3.78 (m, 4H), 3.10(s, 3H), 2.26–2.03 (m, 4H).

4. 4-(2,3-Difluoro-5-hydroxyphenyl)-4-methoxy-3,4,5,6-tetrahydro-2H-pyran

Prepared from 3,4-difluorophenol.

MW: 244.26

$^1$H NMR (CDCl$_3$) δ:6.70–6.50(m, 2H), 3.98–3.76(m, 4H), 3.11(s, 3H), 2.25–2.00(m, 4H).

5. 4-(2,6-Difluoro-3-hydroxyphenyl)-4-methoxy-3,4,5,6-tetrahydro-2H-pyran

Prepared from 2,4-difluorophenol.

MW: 244.26

$^1$H NMR (CDCl$_3$) δ:6.94(ddd, J=4.8, 9.2, 9.2 Hz, 1H), 6.78(ddd, J=2.2, 9.2, 11.3 Hz, 1H), 5.24(d, J=6.23 Hz, 1H), 4.00–3.70(m, 4H), 3.13(s, 3H), 2.39–2.17(m, 4H).

6. 4-(4-Hydroxyphenyl)-4-methoxy-3,4,5,6-tetrahydro-2H-pyran

Prepared from 4-bromophenol.

MW: 208.28

$^1$H NMR (CDCl$_3$) δ:7.30–7.21 (m, 2H), 6.87–6.78(m, 2H), 5.45(s, 1H), 3.95–3.76(m,4H), 2.95(s, 3H), 2.11–1.90 (m, 4H).

EXAMPLE 47

4(3-Hydroxy-5-fluorophenyl)-4-methylsulfinyl-3,4,5,6-tetrahydro-2H-pyran

To a stirred solution of 4-(3-hydroxy-5-fluorophenyl)-4-methylthio-3,4,5,6-tetrahydro-2H-pyran (749 mg, 3.1 mmol)(EP 462830 A2 (1991)) in methanol-water (1:1.v/v; 20 ml) cooled to 0° C. was added NaIO$_4$ (710 mg, 3.3 mmol), the ice bath removed and the mixture stirred at room temperature for 2 hours. The reaction mixture was poured into water (50 ml) and extracted with ethyl acetate (50 ml). The organic extract was washed with water (50 ml), brine (50 ml), dried (MgSO$_4$) and concentrated in vacuo. The residual solids were purified by column chromatography on silica gel (SiO$_2$, 150 g; ethyl acetate) to afford 752 mg (94%) of the titled compound as white solids.

$^1$H-NMR (CDCl$_3$) δ:8.93 (s, 1H), 6.77 (s, 1H), 6.60 (d, J=9.9 Hz, 1H), 6.53 (d, J=10.3 Hz, 1H), 4.09–3.88 (m, 2H), 3.66–3.48 (m, 2H), 2.50–2.29 (m, 2H), 2.20–2.00 (m, 2H), 2.06 (s, 3 H).

EXAMPLE 48

4-5-Fluoro(3-hydroxyphenyl)-4-methylsulfonyl-3,4,5,6-tetrahydro-2H-pyran

To a stirred solution of 4-(5-fluoro-3-hydroxyphenyl)-4-methylthio-3,4,5,6-tetrahydro-2H-pyran (660 mg, 2.7 mmol) in chloroform (20 ml) was added mCPBA (1.48 g, 6.0 mmol) and the mixture stirred at room temperature overnight. To the reaction mixture was added calcium hydroxide (3 mmol) and the reaction mixture stirred vigorously. Insolubles were removed by filtration and the filtrate concentrated. The residual solids were purified by column chromatography on silica gel (SiO$_2$, 150 g; hexane/ethyl acetate (1:2)) to afford 545 mg (81%) of the titled compound as white solids.

$^1$H-NMR (CDCl$_3$) δ:6.86 (dd, J=2.2, 2.2 Hz, 1H), 6.82 (ddd, J=10.2, 2.2, 2.2 Hz, 1H), 6.64 (ddd, J=9.5, 2.2, 2.2 Hz, 1H), 5.55 (s, 1H), 4.08–3.97 (m, 2H), 3.49–3.36 (m, 2H), 2.66–2.50 (m, 2H), 2.53 (s, 3H), 2.41–2.30 (m, 2H).

EXAMPLE 49

The following (1-imidazolyl)benzyl alcohols were synthesized from appropriate starting materials in a similar manner to that described in Example 2 (for aldehydes), Example 4 (for nitriles) or Example 25 (for esters).

1. 2-Chloro-4-(2-methylimidazol-1-yl)benzyl alcohol

Prepared from 2-methylimidazole and ethyl 2-chloro-4-fluorobenzoate.

MW: 222.67

¹H NMR(CDCl₃) δ:7.69 (d, J=8 Hz, 1H), 7.32 (d, J=2 Hz, 1H), 7.24 (dd, J=8, 2 Hz, 1H), 7.01 (d, J=1 Hz, 1H), 6.99 (d, J=1 Hz, 1H), 4.86 (s, 2H), 3.1 (br, 1H), 2.36 (s, 3H).

2. 3-Methyl-4-(2-methylimidazol-1-yl)benzyl alcohol

Prepared from 2-methylimidazole and ethyl 4-fluoro-3-methylbenzoate.

MW: 202.26

¹H NMR (CDCl₃) δ:7.37 (br, 1H), 7.31 (d, J=8 Hz, 1H), 7.17 (d, J=8 Hz, 1H), 7.04 (d, J=1 Hz, 1H), 6.86 (d, J=1 Hz, 1H), 4.76 (s, 2H), 2.17 (s, 3H), 2.05 (s, 3H).

3. 3-Fluoro(2-methylimidazol-1-yl)benzyl alcohol

Prepared from 2-methylimidazole and ethyl 3,4-difluorobenzoate.

MW: 206.22

₁H NMR(CDCl₃) δ: 7.2–7.4 (m, 3H), 7.03 (d, J=1 Hz, 1H), 6.95 (br, 1H), 4.80 (s, 2H), 3.3 (br, 1H), 2.28 (s, 3H).

4. 2-Methyl-4-(2-methylimidazol-1-yl)benzyl alcohol

Prepared from 2-methylimidazole and ethyl 4-fluoro-2-methylbenzoate.

MW: 202.26

¹H NMR (CDCl₃)δ: 7.51 (d, J=8 Hz, 1H), 7.1–7.2 (m, 2H), 7.00 (d, J=1 Hz, 1H), 6.97 (d, J=1 Hz, 1H), 4.77(s, 2H), 2.40 (s, 3H), 2.35 (s, 3H).

5. 4-(2-Methylimidazol-1-yl)-2-trifluoromethylbenzyl alcohol

Prepared from 2-methylimidazole and ethyl 4-fluoro-2-trifluoromethyl benzoate.

MW: 256.23

¹H NMR (CDCl₃) δ: 7.93 (d, J=8 Hz, 1H), 7.6 (br, 1H), 7.53 (d, J=8 Hz, 1H), 7.05 (d, J=1 Hz, 1H), 7.02 (d, J=1 Hz, 1H), 4.98 (s, 2H), 2.37 (s, 3H).

6. 2-Fluoro-4-(2-methylimidazol-1-yl)benzyl alcohol

Prepared from 2-methylimidazole and ethyl 2,4-difluorobenzoate.

MW: 206.22

¹H NMR (CDCl₃) δ: 7.60 (dd, J=8, 8 Hz, 1H), 7.14 (dd, J=8, 2 Hz, 1H), 7.03 (dd, J=10, 2 Hz, 1H), 7.05 (d, J=1 Hz, 1H), 6.99 (d, J=1 Hz, 1H), 4.85 (s, 2H), 2.6 (br, 1H), 2.38 (s, 3H).

7. 2-Methoxy-4-(2-methylimidazol-1-yl)benzyl alcohol

Prepared from 2-methylimidazole and ethyl 2-methoxy-4-fluorobenzoate.

MW: 218.25

¹H NMR (CDCl₃) δ: 7.43 (d, J=8 Hz, 1H), 7.02 (d, J=1 Hz, 1H), 7.00 (d, J=1 Hz, 1H), 6.88 (dd, J=8, 2Hz, 1H), 6.78 (d, J=2 Hz, 1H), 4.74 (s, 2H), 3.89 (s, 3H), 2.7 (br, 1H), 2.36 (s, 3H).

8. 4-(4-Methylimidazol-1-yl)benzyl alcohol

Prepared from 4-methylimidazole and ethyl 4-fluorobenzoate.

MW: 250.30

¹H NMR (CDCl₃) δ: 7.65 (br, 1H), 7.4–7.5 (m, 2H), 7.3–7.4 (m, 2H), 7.0 (br, 1H), 4.8 (s, 2H), 2.3 (s, 3H).

9. 4-(4-Phenylimidazol-1-yl)benzyl alcohol

Prepared from 4-phenylimidazole and 4-fluorobenzaldehyde.

¹H NMR (CDCl₃) δ: 7.8–7.9 (m, 3H), 7.4–7.6 (m, 7H), 7.25–7.3 (m, 1H) 4.8 (br, 2H).

10. 4-(2-Ethylimidazol-1-yl)benzyl alcohol

Prepared from 2-ethylinmidazole and ethyl 4-fluorobenzoate.

MW: 202.26

¹H NMR (CDCl₃) δ7.50 (d, J=8 Hz, 2H), 7.28 (d, J=8 Hz, 2H), 7.02 (d,J=1 Hz, 1H), 6.97 (d, J=1 Hz, 1H), 4.80 (s, 2H), 2.63 (dq, J=1, 8 Hz, 2H), 1.23 (dt, J=3, 8 Hz, 3H).

11. 4-(2-Propylimidazol-1-yl)benzyl alcohol

Prepared from 2-propylimidazol and ethyl 4-fluorobenzoate.

MW: 216.29

¹H NMR (CDCl₃) δ: 7.60–7.80(m, 6H), 4.80(s, 2H), 2.70–2.45 (m, 2H), 2.00–1.50(m, 3H), 1.00–0.70(m, 3H).

12. 4-(2-Isopropylimidazol-1-yl)benzyl alcohol

Prepared from 2-isopropylimidazol and ethyl 4-fluorobenzoate.

MW: 216.29

¹H NMR (CDCl₃) δ:7.55–6.80(m, 6H), 4.79(s, 2H), 3.07–2.85 (m, 1H), 2.37(b 1H), 1.24(d, J=6.9 Hz, 6H).

13. 4-(2-Benzylimidazol-1-yl)benzyl alcohol

Prepared from 2-benzylimidazol and ethyl 4-fluorobenzoate.

MW: 264.33

¹H NMR (CDCl₃) δ:7.45–7.37(m, 2H), 7.28–7.10(m, 8H), 7.00(d, J=1.5 Hz, 1H), 4.77(d, J=4.0 Hz, 2H), 4.02(s, 2H), 2.20–2.07(br, 1H).

14. 4-[2-(Pyridin-2-yl)imidazol-1-yl]benzyl alcohol

Prepared from 2-(pyridin-2-yl)imidazole and 4-fluorobenzonitrile.

MW: 251.28

¹H NMR (CDCl₃) δ:8.36–8.27(m, 1H), 7.89(d, J=8.1 Hz, 1H), 7.70(dd, J=1.8, 8.1 Hz, 1H), 7.39(d, J=8.8 Hz, 2H), 7.30–7.07(m, 5H), 4.76(d, J=4.8 Hz, 2H), 2.07(br, 1H).

15. 4-(2-Trifluroethylimidizol-1-yl)benzyl alcohol

Prepared from 2-trifluoromethylimidazole and 4-trifluorobenzonitrile.

MW: 242.2

¹H NMR(CDCl₃) δ:7.55–7.05(m, 6H), 4.80(br d, 2H), 1.95(br t, 1H).

EXAMPLE 50

3-(2-Methylimidazol-1-yl)benzyl alcohol a. 3-(2-Methylimidazol-1-yl)benzonitrile To a stirred solution of 2-methylimidazole (25 g, 0.3 mol) and 3-bromobenzo-nitrile (55 g, 0.3 mol) in pyridine (60 mL) was added $K_2CO_3$ (42 g), CuO (1.5 g), Cu powder (1.5 g) and CuBr (1.5 g) under a nitrogen atmosphere. The resulting mixture was heated at reflux temperature for 64 hr. The reaction mixture was filtered through a pad of celite and the filtrate was concentrated in vacuo. The residue was purified by column chromatography on silica gel eluting with dichloromethane-methanol (10:1) to afford 12.9 g (23%) of 3-(2-methylimidazol-1-yl)benzonitrile as white solids.

¹H-NMR (CDCl₃) δ:7.80–7.63(m, 4H), 7.07(d, J=1.5 Hz, 1H), 7.02 (d, J=1.5 Hz, 1H), 2.39(s, 3H).

b. 3-(2-Methylimidazol-1-yl)benzyl alcohol 3-(2-Methylimidazol-1-yl)benzonitrile was reduced to 3-(2-methylimidazol-1-yl)-benzyl alcohol using diisobutylaluminum hydride according to the procedure of Example 4, Part b.

MW: 188.23

¹H NMR (CDCl₃) δ: 7.51–7.15(m, 4H), 7.00(s, 2H), 4.79(s, 2H), 2.34(s, 3H).

EXAMPLE 51

The following compounds of the invention were prepared substantially according to the methods previously described.

1. 4-Methoxy-4-[3-[4-(2-methylimidazol-1-yl) benzylthio]-phenyl]-3,4,5,6-tetrahydro-2H-pyran

MW: 394.54 mp: 95.5°–96° C.

IR: (KBr) n 1518, 1421, 1303, 1070, 762 cm$^{-1}$. $^1$H NMR: (DMSO-d$_6$) δ7.38 (d, J=8 Hz, 2H), 7.33–7.23 (m, 4H), 7.20 (d, J=8 Hz, 2H), 7.02 (d, J=1 Hz, 1H), 6.97 (d, J=1 Hz, 1H), 4.16 (s, 2H), 3.85–3.79 (m, 4H), 2.93 (s, 3H), 2.34 (s, 3H), 1.95–1.90 (m, 4H).

2. 4-Methoxy-4-[3-[4-(2-methylimidazol-1-yl) benzyloxy]-5-trifluoromethyl-phenyl]-3,4,5,6-tetrahydro-2H-pyran

MW: 446.47 mp: 148°–150° C. (decompose)

IR: (KBr) n 1605, 1520, 1350, 1300, 1135 cm$^{-1}$.

$^1$H NMR: (DMSO-d$_6$) δ7.64 (d, J=8.4 Hz, 2H), 7.49 (d, J=8.4 Hz, 2H), 7.36–7.22 (m, 4H), 6.92 (d, J=1.5 Hz, 1H), 5.30 (s, 2H), 3.80 (m, 4H), 2.89 (s, 3 H), 2.29 (s, 3H), 2.05–1.85 (m, 4H).

3. 4-[2-Fluoro-5-methoxy-3-[4-(2-methylimidazol-1-yl) benzyloxy]phenyl]-4-methoxy-3,4,5,6-tetrahydro-2H-pyran hyrdochloride

MW: 462.95 mp: 211.3°–212.2° C.

IR: (KBr) n 3070, 2980, 2960, 2880, 2590, 1600, 1525, 1490, 1445, 1430, 1210, 1170, 1100, 1160 cm$^{-1}$.

$^1$H NMR: (DMSO-d$_6$) δ7.90 (d, J=1.8 Hz, 1H); 7.78 (d, J=1.8 Hz, 1H), 7.74 (d, J=8.4 Hz, 2H), 7.68 (d, J=8.4 Hz, 2H), 6.85 (dd, J=6.6, 2.9 Hz, 1H), 6.44 (dd, J=5.1, 2.9 Hz, 1H), 5.29 (s, 2H), 3.76 (s, 3H), 3.75–3.61 (m, 4 H), 2.98 (s, 3H), 2.56 (s, 3H), 2.12–1.92 (m, 4H).

4. 4-[5-Chloro-2-fluoro-3-[4-(2-methylimidazol-1-yl) benzyloxy]phenyl]-4-methoxy-3,4,5-tetrahydro-2H-pyran hydrochloride

MW: 467.37 mp: >200° C.

IR: (KBr) n 1525, 1475, 1430, 1210 cm$^{-1}$.

$^1$H NMR: (DMSO-d$_6$) δ7.90 (d, J=2.2 Hz, 1H), 7.80–7.62 (m, 5H), 7.42 (dd,J=2.6, 7.0 Hz, 1H), 6.97 (dd, J=2.2, 5.9 Hz, 1H), 5.32 (s, 2H), 3.77–3.59 (m, 4H), 2.98 (s, 3H), 2.55 (s, 3H), 2.10–1.90 (m, 4H).

5. 4-[2-Fluoro-5-methyl-3-[4-(2-methylimidizol-1-yl) benzyloxy]phenyl]-4-methoxy-3,4,5,6-tetrahydro-2H-pyran hydrochloride

MW: 446.95 mp: >200° C.

IR: (KBr) n 1600, 1525, 1325, 1105 cm$^{-1}$.

$^1$H NMR: (DMSO-d$_6$)δ:7.89 (d, J=2.2 Hz, 1H), 7.81–7.62 (m, 5H), 7.15–7.05 (m, 1H), 6.80–7.72 (m, 1H), 5.25 (s, 2H), 3.80–3.60 (m, 4H), 2.95 (s, 3 H), 2.55 (s, 3H), 2.30 (s, 3H), 2.11–1.89 (m, 4H).

6. 4-[2-Fluoro-3-[4-(2-methylimidazol-1-yl)benzyloxy]-5-trifluoromethy]phenyl-4-methoxy-3,4,5,6-tetrahydro-2H-pyran hydrochloride

MW: 500.29 mp: 239°–240° C. (decompose)

IR: (KBr) n 1525, 1442, 1368, 1308, 1215, 1118 cm$^{-1}$.

$^1$H NMR: (DMSO-d$_6$) δ7.85 (d, J=2 Hz, 1H), 7.75 (d, J=8 Hz, 2H), 7.6–7.7 (m, 4H), 7.2–7.3 (m, 1H), 5.39 (s, 2H), 3.7 (br, 4H), 2.99 (s, 3H), 2.1 (br, 4 H).

We claim:

1. A compound of the formula

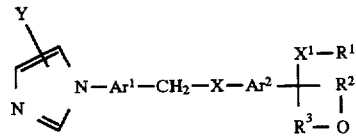

and the pharmaceutically-acceptable salts thereof, wherein

Y is hydrogen, $C_1$–$C_8$ alkyl, halosubstituted $C_1$–$C_4$ alkyl, phenyl, substituted phenyl, $C_7$–$C14$ phenylalkyl, $C_7$–$C_{14}$ (substituted phenyl)alkyl, pyridyl, substituted pyridyl, $C_6$–$C_{13}$ pyridylalkyl or $C_6$–$C_{13}$ (substituted pyridyl)alkyl, wherein each substituent is independently halo, nitro, cyano, $C_1$–$C_4$ alkyl, $C_1$–$C_4$ alkoxy, halosubstituted $C_1$–$C_4$ alkyl, halosubstituted $C_1$–$C_4$ alkoxy, $NR^4R^5$, $CO_2R^4$ or $CONR^4R^5$, wherein $R^4$ and $R^5$ are each, independently, hydrogen or $C_1$–$C_6$ alkyl;

$Ar^1$ and $Ar^9$ are each, independently, phenylene, monosubstituted phenylene or di-substituted phenylene, wherein the substituents are, independently, halo, $C_1$–$C_4$ alkyl, $C_1$–$C_4$ alkoxy, halo-substituted $C_1$–$C_4$ alkyl or halo-substituted $C_1$–$C_4$ alkoxy;

X and $X^1$ are each, independently, O, S, SO or $SO_2$;

$R^1$ is hydrogen or $C_1$–$C_4$ alkyl; and $R^2$ and $R^3$ are each, independently, methylene, ethylene or propylene.

2. A compound according to claim 1, wherein $Ar^1$ and $Ar^2$ are each phenylene or mono-substituted phenylene; and $X^1$ is O.

3. A compound according to claim 2, wherein $Ar^1$ is 1,4-phenylene or mono-substituted 1,4-phenylene and $Ar^2$ is 1,3-phenylene or mono-substituted 1,3-phenylene.

4. A compound according to claim 3, wherein X is O or S; $R^2$ and $R^3$ are each ethylene; and Y is at the 2-position of the imidazole ring.

5. A compound according to claim 4, wherein $Ar^1$ is 1,4-phenylene or 2-fluoro-1,4-phenylene; $Ar^2$ is 1,3-phenylene, 2-fluoro-1,3-phenylene or 5-fluoro-1,3-phenylene; X is O; $R^1$ is methyl; and Y is alkyl.

6. A compound according to claim 5, wherein Y is methyl.

7. A compound according to claim 1, wherein $Ar^1$ is 1,4-phenylene or mono-substituted 1,4-phenylene and $Ar^2$ is 2,5-difluoro-1,3-phenylene.

8. A compound according to claim 7, wherein Y is alkyl at the 2-position of the imidazole ring; X and $X^1$ are each O; $R^1$ is methyl; and $R^2$ and $R^3$ are each ethylene.

9. A compound according to claim 8, wherein Y is methyl.

10. A compound according to claim 1, selected from the group consisting of:

4-Methoxy-4-[3-[4-(2-methylimidazol-1-yl)benzyloxy] phenyl]-3,4,5,6-tetrahydro-2H-pyran;

4-[5-Fluoro-3-[4-(2-methylimidazol-1-yl)benzyloxy] phenyl]-4-methoxy-3,4,5,6-tetrahydro-2H-pyran;

4-[3-[2-Fluoro-4-(2-methylimidazol-1-yl)benzyloxy] phenyl]-4-methoxy-3,4,5,6-tetrahydro-2H-pyran;

4-[5-Fluoro-3-[4-(2-methylimidazol-1-yl)benzyloxy] phenyl]-4-methylthio-3,4,5,6-tetrahydro-2H-pyran; and 4-[2,5-Difluoro-3-[4-(2-methylimidazol-1-yl)benzyloxy] phenyl]-4-methoxy-3,4,5,6-tetrahydro-2H-pyran.

11. 4-[5-Fluoro-3-[4-(2-methylimidazol-1-yl)benzyloxy] phenyl]-4-methoxy-3,4,5,6-tetrahydro-2H-pyran, a compound according to claim 1.

12. 4-[5-Fluoro-3-[4-(2-methylimidazol-1-yl)benzyloxy]phenyl]-4-methoxy-3,4,5,6-tetrahydro-2H-pyran hydrochloride, a compound according to claim 1.

13. A pharmaceutical composition for the treatment of allergic or inflammatory conditions in a mammalian subject which comprises a therapeutically effective amount of a compound of claim 1 and a pharmaceutically acceptable carrier.

14. A method for the treatment of a medical condition for which a lipoxygenase inhibitor is needed, in a mammalian subject, which comprises administering to said subject a therapeutically effective amount of a compound according to claim 1.

15. A method according to claim 14, wherein the medical condition is an allergic or inflammatory condition.

* * * * *